US012757860B2

(12) United States Patent
Peleg et al.

(10) Patent No.: US 12,757,860 B2
(45) Date of Patent: Oct. 13, 2026

(54) SESAME PLANTS RESISTANT TO ACETOLACTATE SYNTHASE-INHIBITING HERBICIDES, COMPOSITIONS AND METHODS FOR PRODUCING SAME

(71) Applicant: Yissum Research Development Company of The Hebrew University of Jerusalem Ltd., Jerusalem (IL)

(72) Inventors: Zvi Peleg, Moshav Herut (IL); Yaron Gadri, Kibbutz Shamir (IL); Asaf Avneri, Moshav Kohav (IL)

(73) Assignee: YISSUM RESEARCH DEVELOPMENT COMPANY OF THE HEBREW UNIVERSITY OF JERUSALEM LTD., Jerusalem (IL)

( * ) Notice: Subject to any disclaimer, the term of this patent is extended or adjusted under 35 U.S.C. 154(b) by 71 days.

(21) Appl. No.: 18/568,266

(22) PCT Filed: Jun. 8, 2022

(86) PCT No.: PCT/IL2022/050607
§ 371 (c)(1),
(2) Date: Dec. 7, 2023

(87) PCT Pub. No.: WO2022/259249
PCT Pub. Date: Dec. 15, 2022

(65) Prior Publication Data

US 2024/0298601 A1 Sep. 12, 2024

Related U.S. Application Data

(60) Provisional application No. 63/208,007, filed on Jun. 8, 2021.

(51) Int. Cl.
*C12N 15/82* (2006.01)
*A01H 6/66* (2018.01)
(Continued)

(52) U.S. Cl.
CPC ............. *A01H 6/66* (2018.05); *C12N 9/1022* (2013.01); *C12N 15/8274* (2013.01);
(Continued)

(58) Field of Classification Search
None
See application file for complete search history.

(56) References Cited

U.S. PATENT DOCUMENTS 5,605,011 A 2/1997 Bedbrook
10,017,827 B2 * 7/2018 Sala ..................... C12Q 1/6895
(Continued)

FOREIGN PATENT DOCUMENTS

CN 107267480 A * 10/2017 ..... C12Y 202/01006
WO 2006094084 A2 9/2006
(Continued)

OTHER PUBLICATIONS

Zhang, Lulu, et al. "Mutations in target gene confers resistance to acetolactate synthase inhibitors in Echinochloa phyllopogon." Plant Physiology and Biochemistry 216 (2024): 109194. (Year: 2024).*
(Continued)

*Primary Examiner* — Weihua Fan
(74) *Attorney, Agent, or Firm* — FULLER IP LAW LLC; Rodney J. Fuller

(57) ABSTRACT

The present invention relates to sesame plants resistant to herbicides that inhibit the plant enzyme acetolactate synthase (ALS), and further to compositions and methods for producing the same.

17 Claims, 21 Drawing Sheets

Specification includes a Sequence Listing.

(51) Int. Cl.
*C12N 9/10* (2006.01)
*C12Q 1/6895* (2018.01)

(52) U.S. Cl.
CPC ....... *C12Q 1/6895* (2013.01); *C12Q 2600/13* (2013.01); *C12Y 202/01006* (2013.01)

(56) References Cited

U.S. PATENT DOCUMENTS

| | | | |
|---|---|---|---|
| 10,865,406 | B2 | 12/2020 | Hain |
| 2003/0097692 | A1 | 5/2003 | Jander |

FOREIGN PATENT DOCUMENTS

| | | | |
|---|---|---|---|
| WO | 2007149069 | A2 | 12/2007 |
| WO | 2008124495 | A2 | 10/2008 |
| WO | 2012049268 | A1 | 4/2012 |

OTHER PUBLICATIONS

Duggleby, Ronald G., et al. "Systematic characterization of mutations in yeast acetohydroxyacid synthase: interpretation of herbicide-resistance data." European Journal of Biochemistry 270.13 (2003): 2895-2904. (Year: 2003).*
NCBI Reference Sequence: XP_011073073.1 (Year: 2017).*
Channaoui et al., (2019) Development and evaluation of diverse promising rapeseed (*Brassica napus* L.) mutants using physical and chemical mutagens. OCL 26: 35.
Dor et al., (2016) Characterization of the novel tomato mutant HRT, resistant to acetolactate synthase-inhibiting herbicides. Weed Science 64(2): 348-360.
Duary and Hazra (2013) Determination of critical period of crop-weed competition in sesame. Indian Journal of Weed Science 45(4): 253-256.
Gadri et al., (2020) Tradeoffs between yield components promote crop stability in sesame. Plant Sci 295: 110105. 7 pages.
Gala et al., (2013) Estimation of critical period for weed control in sesame (*Sesamum indicum* L.). Assiut Journal of Agricultural Sciences 44(3): 32-45. Abstract.
Ghanizadeh et al., (2019) The genetic inheritance of herbicide resistance in weeds. Critical Reviews in Plant Sciences 38(4): 295-312.
Henikoff and Henikoff (1992) Amino acid substitution matrices from protein blocks. Proc Natl Acad Sci U S A 89(22): 10915-10919.
Imaizumi et al., (2008) Genetic diversity of sulfonylurea-resistant and-susceptible Monochoria vaginalis populations in Japan. Weed Research 48(2): 187-196.
Jander et al., (2003) Ethylmethanesulfonate saturation mutagenesis in *Arabidopsis* to determine frequency of herbicide resistance. Plant Physiol 131(1): 139-146.
Karnas et al., (2019) Critical period for weed control in sesame production. Weed Biology and Management 19(4): 121-128.
Kolkman et al., (2004) Acetohydroxyacid synthase mutations conferring resistance to imidazolinone or sulfonylurea herbicides in sunflower. Theor Appl Genet 109(6): 1147-1159.
Kouighat et al., (2021) Novel genetic variability in sesame induced via ethyl methane sulfonate. Journal of Crop Improvement 35(5): 654-665.
Kumar et al., (2018) Recent approaches for herbicide resistance management in weeds: A review. International Journal of Chemical Studies 6(4): 2844-2850.
Langham et al., (2007) Review of herbicide research on sesame (*Sesamum indicum* L.). Version 1, American Sesame Growers Association (ASGA), Gainesville, FL, USA. 196 pages.
Langham et al., (2018) XVI. Sesame Weed Control—Part 1, (*Sesamum indicum* L.). Working Paper 1. Sesame Research LLC. DOI:10.13140/RG.2.2.21216.94722. 201 pages.
Madeira et al., (2019) The EMBL-EBI search and sequence analysis tools APIs in 2019. Nucleic Acids Res 47(W1): W636-W641.
Patrignani and Ochsner (2015) Canopeo: A powerful new tool for measuring fractional green canopy cover. Agronomy Journal 107(6): 2312-2320.
Russell et al., (2002) Sulfonylurea herbicides. Pesticide Outlook 13(4): 166-173.
Sabag et al., (2021) Genome-wide association analysis uncovers the genetic architecture of tradeoff between flowering date and yield components in sesame. BMC Plant Biol 21(1): 549.
Sebastian et al., (1989) Semidominant soybean mutation for resistance to sulfonylurea herbicides. Crop Science 29(6): 1403-1408.
Singh et al., (1992) Investation by weeds and their management in oilseed crops. Agricultural Reviews 13(3): 163-175.
Tan et al., (2005) Imidazolinone-tolerant crops: history, current status and future. Pest Manag Sci 61(3): 246-257.
Teboul et al., (2020) Genetic Architecture Underpinning Yield Components and Seed Mineral-Nutrients in Sesame. Genes (Basel) 11(10): 1221.
Umbarger (1978) Amino acid biosynthesis and its regulation. Annu Rev Biochem 47: 533-606.
Vasanthan et al., (2019) Study on effect of nipping and foliar spray on seed yield of sesame var. TMV 7. International Journal of Chemical Studies 7(3): 4180-4183.
Vilan Itamar (2017) Effect of Sowing Date on Development in Sesame (*Sesamum indicum* L.). M.Sc. Thesis. Submitted to the Robert H. Smith Faculty of Agriculture, Food and Environment, The Hebrew University of Jerusalem, Israel. 51 pages. English abstract on pages i-iii.
Wang et al., (2014) Genome sequencing of the high oil crop sesame provides insight into oil biosynthesis. Genome Biol 15(2): R39.
Yu and Powles (2014) Resistance to AHAS inhibitor herbicides: current understanding. Pest Manag Sci 70(9): 1340-1350.
Yu et al., (2010) AHAS herbicide resistance endowing mutations: effect on AHAS functionality and plant growth. J Exp Bot 61(14): 3925-3934.
Database UniProt [Online] Oct. 7, 2020 (Oct. 7, 2020), "RecName: Full=Acetolactate synthase (ECO:0000256| ARBA:ARBA00013145, ECO:0000256|RuleBase:RU003591); EC=2.2.1.6 (ECO:0000256| ARBA:ARBA00013145, ECO:0000256|RuleBase: RU003591);", XP002807455. Retrieved from EBI accession No. UniProt: A0A619SSR8. Database accession No. A0A619SSR8. 2 pages.
"How to Control Broadleaf Weeds in Sesame Fields," Agricultural Materials Guide, Farmers' Consultant. Zhang Man, editor of the "Scientific Farming " col. p. 22, date: Dec 31, 2015 (Dec 31, 2015). With machine translation. 2 pages.

* cited by examiner

Foramsulfuron

Florasulam

Fig. 9D
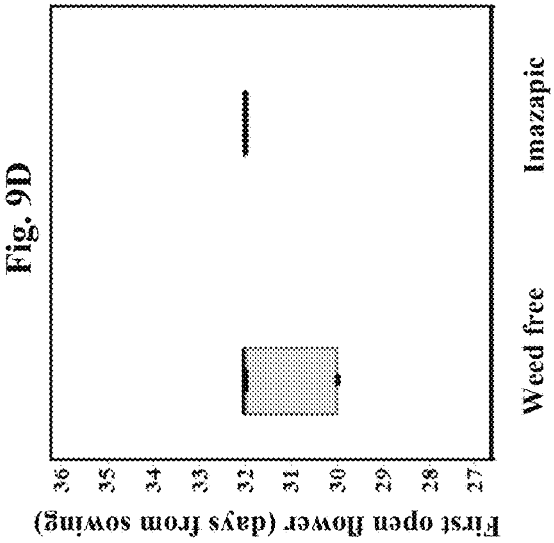
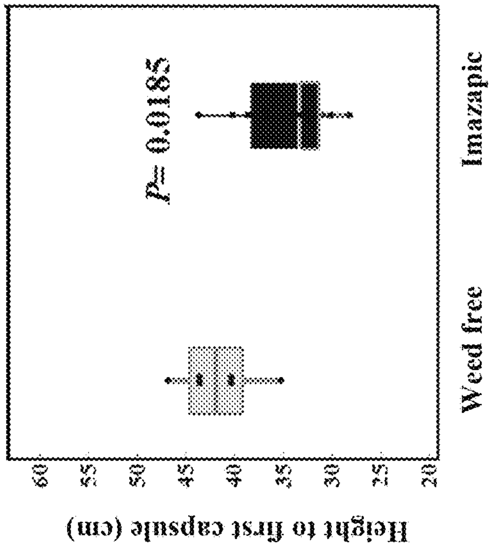
Fig. 9E
Fig. 9F
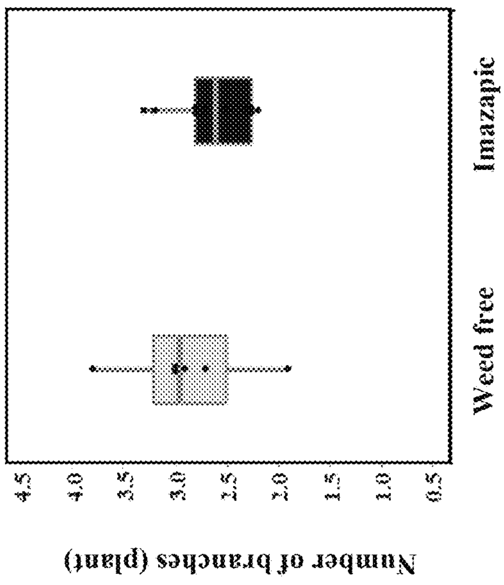
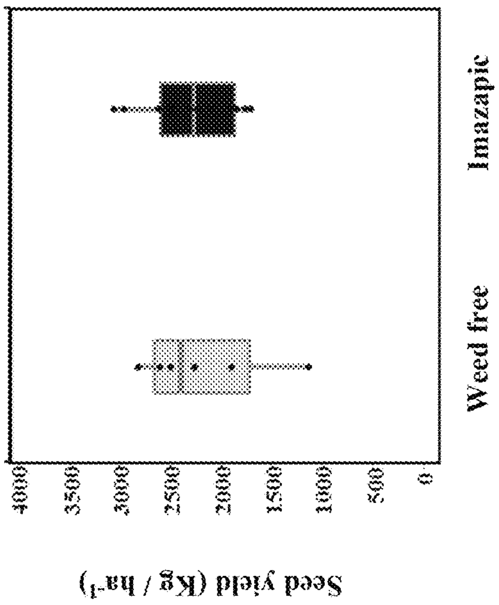
Fig. 9G

SEQUENCE LISTING

```
<160> NUMBER OF SEQ ID NOS: 15

<210> SEQ ID NO 1
<211> LENGTH: 656
<212> TYPE: PRT
<213> ORGANISM: Sesamum indicum

<400> SEQUENCE: 1

Met Ala Ala Ala Thr Pro Ala Ser Ser Ser Ser Thr Val Trp Lys Arg
1               5                   10                  15
```

-continued

```
Ser Ser Phe Ser Asn Ser Ser Lys Leu Leu Ser Arg Phe Thr Val Pro
            20                  25                  30

Phe Pro His Asn Pro Gln Lys Pro Thr Ala Gly Val Ile Ser Gln Arg
        35                  40                  45

Arg Pro Leu Gln Ile Ser Asn Val Leu Ser Ala Pro Arg Glu Gln Val
    50                  55                  60

His Pro Glu Glu Ala Phe Val Ser Arg Phe Ala Ala Asp Glu Pro Arg
65                  70                  75                  80

Lys Gly Cys Asp Val Leu Val Glu Ala Leu Glu Arg Glu Gly Val Thr
                85                  90                  95

Asp Val Phe Ala Tyr Pro Gly Gly Ala Ser Met Glu Ile His Gln Ala
            100                 105                 110

Leu Thr Arg Ser Lys Ile Ile Arg Asn Val Leu Pro Arg His Glu Gln
        115                 120                 125

Gly Gly Val Phe Ala Ala Glu Gly Tyr Ala Arg Ala Ser Gly Leu Pro
    130                 135                 140

Gly Val Cys Ile Ala Thr Ser Gly Pro Gly Ala Thr Asn Leu Val Ser
145                 150                 155                 160

Gly Leu Ala Asp Ala Leu Leu Asp Ser Val Pro Leu Val Ala Ile Thr
                165                 170                 175

Gly Gln Val Pro Arg Arg Met Ile Gly Thr Asp Ala Phe Gln Glu Thr
            180                 185                 190

Pro Ile Val Glu Val Thr Arg Ser Ile Thr Lys His Asn Tyr Leu Val
        195                 200                 205

Leu Asp Val Glu Asp Ile Pro Arg Val Val Lys Glu Ala Phe Phe Ile
    210                 215                 220

Ala Arg Ser Gly Arg Pro Gly Pro Val Leu Ile Asp Val Pro Lys Asp
225                 230                 235                 240

Ile Gln Gln Gln Met Val Val Pro Asn Trp Asn Gln Pro Met Arg Leu
                245                 250                 255

Ala Gly Tyr Leu Ser Arg Leu Pro Arg Pro Pro Ser Ala Met Leu Leu
            260                 265                 270

Glu Gln Ile Val Arg Leu Ile Ser Glu Ser Lys Lys Pro Val Leu Tyr
        275                 280                 285

Val Gly Gly Gly Cys Leu Asn Ser Ser Glu Glu Leu Arg Arg Phe Val
    290                 295                 300

Glu Leu Thr Gly Ile Pro Val Ala Ser Thr Leu Met Gly Leu Gly Ser
305                 310                 315                 320

Tyr Pro Cys Ser Asp Glu Glu Phe Ala Leu Gln Met Leu Gly Met His
                325                 330                 335

Gly Thr Val Tyr Ala Asn Tyr Ala Val Asp Lys Ser Asp Leu Leu Leu
            340                 345                 350

Ala Phe Gly Val Arg Phe Asp Asp Arg Val Thr Gly Lys Leu Glu Ala
        355                 360                 365

Phe Ala Ser Arg Ala Lys Ile Val His Ile Asp Ile Asp Ser Ala Glu
    370                 375                 380

Ile Gly Lys Asn Lys Gln Pro His Val Ser Ile Cys Ala Asp Met Lys
385                 390                 395                 400

Leu Ala Leu Gln Gly Leu Asn Leu Ile Leu Glu Asp Met Leu Lys Glu
                405                 410                 415

Gly Lys Asn Asn Val Asp Phe Ser Ala Trp Arg Gln Glu Leu Lys Glu
            420                 425                 430
```

-continued

```
Gln Lys Met Asn Phe Pro Leu Ser Phe Lys Thr Phe Glu Asp Ala Ile
        435                 440                 445

Pro Pro Gln Tyr Ala Ile Gln Val Leu Asp Glu Leu Thr Gly Gly Asn
    450                 455                 460

Ala Ile Ile Ser Thr Gly Val Gly Gln His Gln Met Trp Ala Ala Gln
465                 470                 475                 480

Phe Tyr Lys Tyr Asn Lys Pro Arg Gln Trp Leu Thr Ser Gly Gly Leu
                485                 490                 495

Gly Ala Met Gly Phe Gly Leu Pro Ala Ala Ile Gly Ala Ala Val Ala
            500                 505                 510

Arg Pro Asp Ala Val Val Val Asp Ile Asp Gly Asp Gly Ser Phe Ile
        515                 520                 525

Met Asn Val Gln Glu Leu Ala Thr Ile Arg Val Glu Asn Leu Pro Val
    530                 535                 540

Lys Ile Met Leu Leu Asn Asn Gln His Leu Gly Met Val Val Gln Trp
545                 550                 555                 560

Glu Asp Arg Phe Tyr Lys Ser Asn Arg Ala His Thr Tyr Leu Gly Asn
                565                 570                 575

Pro Ser Lys Glu Ser Glu Ile Phe Pro Asp Met Leu Lys Phe Ala Glu
            580                 585                 590

Ala Cys Asp Ile Pro Ala Ala Arg Val Thr Lys Lys Asp Asp Leu Arg
        595                 600                 605

Ala Ala Ile Gln Lys Met Leu Asp Thr Pro Gly Pro Tyr Leu Leu Asp
    610                 615                 620

Val Ile Val Pro His Gln Glu His Val Leu Pro Met Ile Pro Ser Gly
625                 630                 635                 640

Gly Ala Phe Lys Asp Val Ile Thr Glu Gly Asp Gly Arg Ile Lys Tyr
                645                 650                 655
```

<210> SEQ ID NO 2
<211> LENGTH: 2394
<212> TYPE: DNA
<213> ORGANISM: Sesamum indicum

<400> SEQUENCE: 2

```
aagggcaatt ccgacatttc cctctgctgc ctcctgaata agttccgcct tccaaatcaa     60

acgtgcttcc cttttcctcg ccacagaaaa ccctaaggag ctacagaccc gccgtcgccg    120

ccgatttgca ttctctaacg tccgtcggaa atggcggccg ctactcctgc ctccagctcg    180

tccactgtgt ggaaacgctc ttctttctct aattcgtcga agcttctttc tagatttacc    240

gtcccgttcc ctcacaatcc tcagaagccc acagctggcg tcatttcgca acgccgtccg    300

ctgcaaatct caaatgtgct gtctgctccc agggaacaag tgcatcctga ggaggcgttt    360

gtttcccgat ttgccgctga cgaacctcgg aagggctgcg acgttttagt ggaggcgctt    420

gaacgagaag gggtcaccga cgtctttgct taccccggag gcgcgtctat ggagatccat    480

caagcgctta cccgctccaa aatcatccgg aacgtgctcc cgcgccacga gcagggaggc    540

gtcttcgctg ccgaggggta cgcccgcgct tccggtcttc ccggcgtctg catcgcgaca    600

tctggccctg gtgccaccaa tttggtctct ggcctcgccg atgctcttct cgatagcgta    660

ccgcttgtgg ctatcacagg ccaggttccc cgtcgtatga tcggcactga tgctttccaa    720

gaaaccccta ttgttgaggt aactaggtcg attaccaagc ataattatct tgttttagat    780

gttgaggata ttcctcgggt tgtcaaggaa gctttcttta tcgctcggtc gggaaggcct    840

ggcccagttt tgattgacgt tccaaaagat attcaacagc aaatggtggt accaaattgg    900
```

```
aatcagccaa tgaggttggc tggttacttg tctagattgc ctaggccgcc tagtgcgatg    960

ttgttggagc agatagttag gctgatatcc gagtccaaaa agccggtact ttatgtcggt   1020

ggtgggtgtt tgaattcaag tgaggagttg aggaggtttg tggagctcac aggaattccg   1080

gttgctagca cgcttatggg tcttggttct tatccttgtt ctgatgagga atttgcgctg   1140

caaatgctgg gtatgcatgg gactgtttat gcaaattatg cagtggacaa gagtgatttg   1200

ttgcttgctt ttggagtcag gtttgatgac cgtgtgacgg gtaagctgga ggcatttgcc   1260

agtcgagcaa agattgtcca cattgacatt gattctgctg agattggaaa gaataagcaa   1320

cctcatgtgt ccatttgtgc cgatatgaag ttagctttgc agggtttgaa cttgatattg   1380

gaagacatgc tgaaagaggg taagaacaat gttgactttt cagcctggag gcaagagtta   1440

aaagagcaga agatgaactt tcctttgagt ttcaagacat ttgaagatgc cattccacct   1500

cagtatgcaa ttcaagttct tgatgaactg acaggaggga atgcaatcat tagtactggt   1560

gttgggcagc atcagatgtg ggctgcacaa ttttataagt ataataagcc acgacagtgg   1620

ttgacatcag gtggtttagg ggcaatgggt ttcggacttc ctgcagcaat tggagctgct   1680

gttgcaagac cagatgcagt tgtagtggat attgatggtg atggaagttt tataatgaac   1740

gtgcaggagt tggccactat ccgggtagag aaccttcctg ttaagattat gttgttaaat   1800

aatcagcact tgggtatggt tgtccagtgg gaagaccgct tctataagtc caacagggca   1860

cacacttatc tcggaaatcc ttccaaagag tcagagattt ttccagatat gttgaagttt   1920

gcagaggctt gtgatatacc tgcagctcgt gtgacaaaga aggatgatct cagggcagca   1980

atacaaaaga tgttggatac tcctgggcca tatttgttgg atgtcattgt accccatcaa   2040

gagcatgtct tgcccatgat tcccagtgga ggagccttta aagacgtgat cacagagggt   2100

gatggaagaa ttaagtattg atgtgaagta cggcagagcg gccatttggt tgtgaaaatt   2160

aggtcgcagc taaagggggt ccaagtttat agttttggct tgtaagttgt gttgtgttct   2220

gacatttgca aggtctgatt gtagtacgtc tgctctttat gcttattggt attcagtgat   2280

acctatgttc atttatcaca ttctgtttaa tctattataa taacggttgg atgctcggct   2340

ctattcatgt attttgataa ttatgtagag aaacgcatcc acctaatttg ttaa         2394
```

```
<210> SEQ ID NO 3
<211> LENGTH: 656
<212> TYPE: PRT
<213> ORGANISM: Artificial Sequence
<220> FEATURE:
<223> OTHER INFORMATION: Mutant acetolactate synthase protein

<400> SEQUENCE: 3

Met Ala Ala Ala Thr Pro Ala Ser Ser Ser Ser Thr Val Trp Lys Arg
1               5                   10                  15

Ser Ser Phe Ser Asn Ser Ser Lys Leu Leu Ser Arg Phe Thr Val Pro
            20                  25                  30

Phe Pro His Asn Pro Gln Lys Pro Thr Ala Gly Val Ile Ser Gln Arg
        35                  40                  45

Arg Pro Leu Gln Ile Ser Asn Val Leu Ser Ala Pro Arg Glu Gln Val
    50                  55                  60

His Pro Glu Glu Ala Phe Val Ser Arg Phe Ala Ala Asp Glu Pro Arg
65                  70                  75                  80

Lys Gly Cys Asp Val Leu Val Glu Ala Leu Glu Arg Glu Gly Val Thr
                85                  90                  95
```

```
Asp Val Phe Ala Tyr Pro Gly Gly Ala Ser Met Glu Ile His Gln Ala
            100                 105                 110

Leu Thr Arg Ser Lys Ile Ile Arg Asn Val Leu Pro Arg His Glu Gln
        115                 120                 125

Gly Gly Val Phe Ala Ala Glu Gly Tyr Ala Arg Ala Ser Gly Leu Pro
    130                 135                 140

Gly Val Cys Ile Ala Thr Ser Gly Pro Gly Ala Thr Asn Leu Val Ser
145                 150                 155                 160

Gly Leu Ala Asp Ala Leu Leu Asp Ser Val Pro Leu Val Ala Ile Thr
                165                 170                 175

Gly Gln Val Pro Arg Arg Met Ile Gly Thr Asp Val Phe Gln Glu Thr
            180                 185                 190

Pro Ile Val Glu Val Thr Arg Ser Ile Thr Lys His Asn Tyr Leu Val
        195                 200                 205

Leu Asp Val Glu Asp Ile Pro Arg Val Val Lys Glu Ala Phe Phe Ile
    210                 215                 220

Ala Arg Ser Gly Arg Pro Gly Pro Val Leu Ile Asp Val Pro Lys Asp
225                 230                 235                 240

Ile Gln Gln Gln Met Val Val Pro Asn Trp Asn Gln Pro Met Arg Leu
                245                 250                 255

Ala Gly Tyr Leu Ser Arg Leu Pro Arg Pro Pro Ser Ala Met Leu Leu
            260                 265                 270

Glu Gln Ile Val Arg Leu Ile Ser Glu Ser Lys Lys Pro Val Leu Tyr
        275                 280                 285

Val Gly Gly Gly Cys Leu Asn Ser Ser Glu Glu Leu Arg Arg Phe Val
    290                 295                 300

Glu Leu Thr Gly Ile Pro Val Ala Ser Thr Leu Met Gly Leu Gly Ser
305                 310                 315                 320

Tyr Pro Cys Ser Asp Glu Glu Phe Ala Leu Gln Met Leu Gly Met His
                325                 330                 335

Gly Thr Val Tyr Ala Asn Tyr Ala Val Asp Lys Ser Asp Leu Leu Leu
            340                 345                 350

Ala Phe Gly Val Arg Phe Asp Asp Arg Val Thr Gly Lys Leu Glu Ala
        355                 360                 365

Phe Ala Ser Arg Ala Lys Ile Val His Ile Asp Ile Asp Ser Ala Glu
    370                 375                 380

Ile Gly Lys Asn Lys Gln Pro His Val Ser Ile Cys Ala Asp Met Lys
385                 390                 395                 400

Leu Ala Leu Gln Gly Leu Asn Leu Ile Leu Glu Asp Met Leu Lys Glu
                405                 410                 415

Gly Lys Asn Asn Val Asp Phe Ser Ala Trp Arg Gln Glu Leu Lys Glu
            420                 425                 430

Gln Lys Met Asn Phe Pro Leu Ser Phe Lys Thr Phe Glu Asp Ala Ile
        435                 440                 445

Pro Pro Gln Tyr Ala Ile Gln Val Leu Asp Glu Leu Thr Gly Gly Asn
    450                 455                 460

Ala Ile Ile Ser Thr Gly Val Gly Gln His Gln Met Trp Ala Ala Gln
465                 470                 475                 480

Phe Tyr Lys Tyr Asn Lys Pro Arg Gln Trp Leu Thr Ser Gly Gly Leu
                485                 490                 495

Gly Ala Met Gly Phe Gly Leu Pro Ala Ala Ile Gly Ala Ala Val Ala
            500                 505                 510

Arg Pro Asp Ala Val Val Val Asp Ile Asp Gly Asp Gly Ser Phe Ile
```

-continued

```
        515                 520                 525

Met Asn Val Gln Glu Leu Ala Thr Ile Arg Val Glu Asn Leu Pro Val
    530                 535                 540

Lys Ile Met Leu Leu Asn Asn Gln His Leu Gly Met Val Val Gln Trp
545                 550                 555                 560

Glu Asp Arg Phe Tyr Lys Ser Asn Arg Ala His Thr Tyr Leu Gly Asn
                565                 570                 575

Pro Ser Lys Glu Ser Glu Ile Phe Pro Asp Met Leu Lys Phe Ala Glu
            580                 585                 590

Ala Cys Asp Ile Pro Ala Ala Arg Val Thr Lys Lys Asp Asp Leu Arg
        595                 600                 605

Ala Ala Ile Gln Lys Met Leu Asp Thr Pro Gly Pro Tyr Leu Leu Asp
    610                 615                 620

Val Ile Val Pro His Gln Glu His Val Leu Pro Met Ile Pro Ser Gly
625                 630                 635                 640

Gly Ala Phe Lys Asp Val Ile Thr Glu Gly Asp Gly Arg Ile Lys Tyr
                645                 650                 655


<210> SEQ ID NO 4
<211> LENGTH: 2394
<212> TYPE: DNA
<213> ORGANISM: Artificial Sequence
<220> FEATURE:
<223> OTHER INFORMATION: Polynucleotide encoding mutant ALS protein

<400> SEQUENCE: 4

aagggcaatt ccgacatttc cctctgctgc ctcctgaata agttccgcct tccaaatcaa     60

acgtgcttcc cttttcctcg ccacagaaaa ccctaaggag ctacagaccc gccgtcgccg    120

ccgatttgca ttctctaacg tccgtcggaa atggcggccg ctactcctgc ctccagctcg    180

tccactgtgt ggaaacgctc ttctttctct aattcgtcga agcttctttc tagatttacc    240

gtcccgttcc ctcacaatcc tcagaagccc acagctggcg tcatttcgca acgccgtccg    300

ctgcaaatct caaatgtgct gtctgctccc agggaacaag tgcatcctga ggaggcgttt    360

gtttcccgat ttgccgctga cgaacctcgg aagggctgcg acgttttagt ggaggcgctt    420

gaacgagaag gggtcaccga cgtctttgct taccccggag gcgcgtctat ggagatccat    480

caagcgctta cccgctccaa aatcatccgg aacgtgctcc cgcgccacga gcagggaggc    540

gtcttcgctg ccgaggggta cgcccgcgct tccggtcttc ccggcgtctg catcgcgaca    600

tctggccctg gtgccaccaa tttggtctct ggcctcgccg atgctcttct cgatagcgta    660

ccgcttgtgg ctatcacagg ccaggttccc cgtcgtatga tcggcactga tgttttccaa    720

gaaaccccta ttgttgaggt aactaggtcg attaccaagc ataattatct tgttttagat    780

gttgaggata ttcctcgggt tgtcaaggaa gctttcttta tcgctcggtc gggaaggcct    840

ggcccagttt tgattgacgt tccaaaagat attcaacagc aaatggtggt accaaattgg    900

aatcagccaa tgaggttggc tggttacttg tctagattgc ctaggccgcc tagtgcgatg    960

ttgttggagc agatagttag gctgatatcc gagtccaaaa agccggtact ttatgtcggt   1020

ggtgggtgtt tgaattcaag tgaggagttg aggaggtttg tggagctcac aggaattccg   1080

gttgctagca cgcttatggg tcttggttct tatccttgtt ctgatgagga atttgcgctg   1140

caaatgctgg gtatgcatgg gactgtttat gcaaattatg cagtggacaa gagtgatttg   1200

ttgcttgctt ttggagtcag gtttgatgac cgtgtgacgg gtaagctgga ggcatttgcc   1260

agtcgagcaa agattgtcca cattgacatt gattctgctg agattggaaa gaataagcaa   1320
```

cctcatgtgt ccatttgtgc cgatatgaag ttagctttgc agggtttgaa cttgatattg 1380
gaagacatgc tgaaagaggg taagaacaat gttgactttt cagcctggag gcaagagtta 1440
aaagagcaga agatgaactt tcctttgagt ttcaagacat ttgaagatgc cattccacct 1500
cagtatgcaa ttcaagttct tgatgaactg acaggaggga atgcaatcat tagtactggt 1560
gttgggcagc atcagatgtg ggctgcacaa ttttataagt ataataagcc acgacagtgg 1620
ttgacatcag gtggtttagg ggcaatgggt ttcggacttc ctgcagcaat tggagctgct 1680
gttgcaagac cagatgcagt tgtagtggat attgatggtg atggaagttt tataatgaac 1740
gtgcaggagt tggccactat ccgggtagag aaccttcctg ttaagattat gttgttaaat 1800
aatcagcact tgggtatggt tgtccagtgg gaagaccgct tctataagtc caacagggca 1860
cacacttatc tcggaaatcc ttccaaagag tcagagattt ttccagatat gttgaagttt 1920
gcagaggctt gtgatatacc tgcagctcgt gtgacaaaga aggatgatct cagggcagca 1980
atacaaaaga tgttggatac tcctgggcca tatttgttgg atgtcattgt accccatcaa 2040
gagcatgtct tgcccatgat tcccagtgga ggagccttta aagacgtgat cacagagggt 2100
gatggaagaa ttaagtattg atgtgaagta cggcagagcg gccatttggt tgtgaaaatt 2160
aggtcgcagc taaagggggt ccaagtttat agttttggct tgtaagttgt gttgtgttct 2220
gacatttgca aggtctgatt gtagtacgtc tgctctttat gcttattggt attcagtgat 2280
acctatgttc atttatcaca ttctgtttaa tctattataa taacggttgg atgctcggct 2340
ctattcatgt attttgataa ttatgtagag aaacgcatcc acctaatttg ttaa 2394

<210> SEQ ID NO 5
<211> LENGTH: 18
<212> TYPE: DNA
<213> ORGANISM: Artificial Sequence
<220> FEATURE:
<223> OTHER INFORMATION: Primer

<400> SEQUENCE: 5
caggttcccc gtcgtatg 18

<210> SEQ ID NO 6
<211> LENGTH: 18
<212> TYPE: DNA
<213> ORGANISM: Artificial Sequence
<220> FEATURE:
<223> OTHER INFORMATION: Primer

<400> SEQUENCE: 6
tccttgacaa cccgagga 18

<210> SEQ ID NO 7
<211> LENGTH: 92
<212> TYPE: DNA
<213> ORGANISM: Artificial Sequence
<220> FEATURE:
<223> OTHER INFORMATION: Nucleic acid marker

<400> SEQUENCE: 7
atcggcactg atgttttcca agaaacccct attgttgagg taactaggtc gattaccaag 60
cataattatc ttgttttaga tgttgaggat at 92

<210> SEQ ID NO 8
<211> LENGTH: 18
<212> TYPE: DNA

<213> ORGANISM: Artificial Sequence
<220> FEATURE:
<223> OTHER INFORMATION: Primer

<400> SEQUENCE: 8
cccactcagc tgcctcat 18

<210> SEQ ID NO 9
<211> LENGTH: 18
<212> TYPE: DNA
<213> ORGANISM: Artificial Sequence
<220> FEATURE:
<223> OTHER INFORMATION: Primer

<400> SEQUENCE: 9
gcgaggccag agaccaaa 18

<210> SEQ ID NO 10
<211> LENGTH: 18
<212> TYPE: DNA
<213> ORGANISM: Artificial Sequence
<220> FEATURE:
<223> OTHER INFORMATION: Primer

<400> SEQUENCE: 10
agggaggtgt cttcgctg 18

<210> SEQ ID NO 11
<211> LENGTH: 18
<212> TYPE: DNA
<213> ORGANISM: Artificial Sequence
<220> FEATURE:
<223> OTHER INFORMATION: Primer

<400> SEQUENCE: 11
cctccagctt acccgtca 18

<210> SEQ ID NO 12
<211> LENGTH: 18
<212> TYPE: DNA
<213> ORGANISM: Artificial Sequence
<220> FEATURE:
<223> OTHER INFORMATION: Primer

<400> SEQUENCE: 12
gctgggtatg catgggac 18

<210> SEQ ID NO 13
<211> LENGTH: 18
<212> TYPE: DNA
<213> ORGANISM: Artificial Sequence
<220> FEATURE:
<223> OTHER INFORMATION: Primer

<400> SEQUENCE: 13
ttgtcacacg agctgcag 18

<210> SEQ ID NO 14
<211> LENGTH: 20
<212> TYPE: DNA
<213> ORGANISM: Artificial Sequence
<220> FEATURE:
<223> OTHER INFORMATION: Primer

<400> SEQUENCE: 14
cagcacttgg gtatggttgt 20

-continued

```
<210> SEQ ID NO 15
<211> LENGTH: 17
<212> TYPE: DNA
<213> ORGANISM: Artificial Sequence
<220> FEATURE:
<223> OTHER INFORMATION: Primer

<400> SEQUENCE: 15

ttcgagtggg atgtgcc                                                        17
```

SESAME PLANTS RESISTANT TO ACETOLACTATE SYNTHASE-INHIBITING HERBICIDES, COMPOSITIONS AND METHODS FOR PRODUCING SAME

CROSS-REFERENCE TO RELATED APPLICATIONS

This application is the U.S. National Stage of International Patent Application No. PCT/IL2022/050607, filed on Jun. 8, 2022, which claims the benefit of and priority to U.S. Provisional Application No. 63/208,007, filed on Jun. 8, 2021, the contents of each of which are hereby incorporated by reference in their entireties.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 20,247 byte ASCII (text) file named "Seq_List" created on Jun. 8, 2022.

FIELD OF THE INVENTION

The present invention relates to herbicide-resistant sesame plants, particularly to sesame plants resistant to herbicides that inhibit the activity of the plant enzyme acetolactate synthase (ALS), and further to compositions and methods for producing same.

BACKGROUND OF THE INVENTION

Sesame (*Sesamum indicum* L.; genome 2n=2x=26), belongs to the *Sesamum* genus of the Padaliaceae family, is an important oil-crop worldwide. Its seeds are used for a wide array of purposes such as the production of oil and Tahini, cooking and baking, and as a source for ingredients used in pharmaceutical products. Sesame seeds are known as one of the best of oil-seeds, since the seeds contain a considerable amount of high-quality oil, proteins, carbohydrates, and a plethora of essential mineral-nutrients (Teboul et al., 2021. Genes, 11:1221). In recent years, the demand for sesame seeds (and secondary products) is increasing as part of the global trends toward healthier plant-based food sources.

However, current sesame seed production is mostly limited to developing countries, using traditional growth practices that are laborious and not cost-effective. Despite its economical and agricultural potential, sesame is an 'orphan crop-plant' with limited research performed in modern genetics and breeding. Thus, it is necessary to bridge the knowledge gap resulting from the current limited production and market as to develop novel cultivars adapted for modern, large-scale agricultural practices.

Weeds infestation is the major biotic factor causing a reduction in sesame plant development and yield production. As a consequence of its slow development during the initial growth stage (Gadri et al., 2020. Plant Science, 295:110105; Langham et al., 2007. Review of herbicide research on sesame (*Sesamum indicum* L.) ASGA, Gainesville, FL, USA), sesame is a poor competitor with weeds. Moreover, its prolonged 'critical period' (i.e., a period in the crop growth cycle during which weeds must be controlled to prevent significant yield losses) further emphasizes the importance of efficient weed control practice. The 'critical period' for sesame has been found to last up to 10 weeks, depending on the growing degree-days and the level of weed infestation (e.g., Aref et al., 2013. Assiut Journal of Agricultural Sciences, 44:32-45; Karnas et al., 2019. Weed Biology and Management, 19:121-128; Vilan 2017. M.Sc. Thesis submitted to The Hebrew University of Jerusalem, Israel). Thus, if weeds are not controlled during this time, it can lead to a severe yield reduction, from about 60% in West Bengal, and 78% in Turkey (Duary and Hazra, 2013. Indian Journal of Weed Science, 45:253-256 and Karnas et al., 2019, ibid, respectively), and up to a complete yield loss (reviewed by Singh et al., 1992. Agricultural Reviews, 13:163-175).

Since their introduction in 1940, chemicals (i.e., herbicides) provides the most cost-effective and efficient practice for weed control. In most major crops, herbicides advantageously enable selective weed control. However, most of the chemical herbicides in use cause some damage to sesame plants. While most modes of action (MOA) of known herbicides (132 herbicides and 58 herbicide combinations) have been tested in almost 40 countries, all of them resulted in yield reduction of sesame (reviewed by Langham et al., 2018. Sesame Weed Control Part 1. Sesame Research LLC, doi: 10.13140/RG.2.2.21216.94722). Some herbicides which are Acetyl CoA Carboxylase (ACCase) inhibitors were found to be safe; however, this group is effective for post-emergence control of grass weeds only.

Among the various herbicide MOAs, a common activity target is Acetolactate synthase (ALS), also known as acetohydroxyacid synthase (AHAS). ALS is a key enzyme catalyzing the initial step in the biosynthesis of branched-chain amino acids including valine, leucine, and isoleucine (Umbarger, 1978. Annual Reviews in Biochemistry, 47:533-606). Inhibition of this enzyme primarily leads to plant starvation, but secondary effects such as the accumulation of 2-ketobutyrate and the distraction of photosynthate transport have also been shown to be involved in plant death (The Imidazoline Herbicides, 1991. Eds: Shaner and O'Connor, CRC Press). ALS inhibiting herbicides control many weed species, have low mammalian toxicity, and are selective in many crops (Yu et al., 2010. Journal of Experimental Botany, 61:3925-3934). The ALS-inhibiting herbicides are divided according to their molecular structure into five chemical classes: Imidazolinones (IMIs), Sulfonylureas (SUs), Pyrimidinyl thiobenzoates (PTBs), Triazolopyrimidines (TPs), and Sulfonylaminocarbonyltriazolinones (SCTs). Imidazolinone and Sulfonylureas are the most widely used classes and include the largest available commercialized herbicides (Saari et al., 1993. In: Resistance to Herbicides in Plants, Eds. S. B. Powles & J. A. M. Holtum. Lewis Publ. CRC Press, Boca Raton, FL). Point-mutation resistance at different sites on the ALS gene were discovered naturally in various weed species (weedscience.org), and were induced in crop-plants (e.g., Tan et al., 2005. Pest Management Science, 61:246-257; International (PCT) Applications Publication No. WO 2007/149069). Additional sources of mutations resulting in herbicide resistance ALS have been described, for example in U.S. Pat. No. 5,605,011; U.S. Patent Application Publication No. 2003/0097692 and International (PCT) Application WO 2012/049268).

Genetic characterization of the resistance mutation has been classified as semi-dominant inheritance, with the heterozygote allele displaying an intermediate resistance (Ghanizadeh et al., 2019. Critical Reviews in Plant Sciences, 38:295-312).

The broad variety of ALS inhibiting herbicides enables the farmers to control a wide range of weed species independently of their growth stages. However, these highly efficient herbicides cannot be used in sesame because conventional sesame plants/commercial sesame varieties are highly susceptible to these ALS inhibiting herbicides.

Thus, there is an urgent need to develop new sesame cultivars with enhanced herbicide resistance, to ensure high production and sustainability.

SUMMARY OF THE INVENTION

The present invention answers the above-described needs, providing sesame plants that are resistant to herbicides inhibiting the activity of acetolactate synthase (ALS). Particularly, the present invention provides sesame plants and parts thereof comprising a mutant ALS gene having a single mutation, said plants having a reduced affinity to at least one ALS-inhibiting herbicide compared to a wild-type *S. indicum*. The sesame plants comprising the mutant ALS gene are tolerant and/or resistant to ALS inhibiting herbicides applied pre-emergence or post-emergence, such that weeds can be controlled throughout the sesame growth period, a significant advantage in agricultural cultivation. Unexpectedly, the resistant sesame plants further exhibited significantly higher yield after being exposed to a treatment, post-emergence, with ALS-inhibiting herbicide compared to the yield obtained when the plants were grown under weed-free conditions (obtained by mechanical or manual weeding). Without wishing to be bound by any specific theory or mechanism of action, the resistance may be attributed to a change in the protein conformation at the herbicide binding site due to a single mutation of alanine to valine substitution, which results in a decreased affinity of the herbicide to the ALS enzyme.

According to certain aspects, the present invention provides a sesame (*Sesamum indicum* L.) plant or a part thereof comprising at least one cell comprising a mutant acetolactate synthase encoding gene (mALS), wherein the mALS encodes a mutant acetolactate synthase (mALS) protein having a reduced affinity to at least one ALS-inhibiting herbicide compared to a wild-type *S. indicum* ALS (SiALS) protein, and wherein the plant is resistant to at least one ALS-inhibiting herbicide.

According to certain embodiments, the wild-type SiALS protein comprises an amino acid sequence having at least 90% identity to the amino acid sequence set forth in SEQ ID NO:1, wherein the amino acid sequence comprises alanine at position 188.

According to certain embodiments, the wild-type SiALS protein comprises an amino acid sequence having at least 95% or more identity to the amino acid sequence set forth in SEQ ID NO:1 wherein the amino acid sequence comprises alanine at position 188.

According to certain exemplary embodiments, the wild-type SiALS protein comprises the amino acid sequence set forth in SEQ ID NO:1.

According to certain embodiments, the mALS protein comprises an amino acid other than alanine at position 188 of a protein having at least 90%, identity to the amino acid sequence set forth in SEQ ID NO:1.

According to certain currently exemplary embodiments, the alanine is substituted by valine (Ala188Val). According to these embodiments, the mALS protein comprises the amino acid valine at position 188 of an amino acid sequence having at least 90% identity to the nucleic acid sequence set forth in SEQ ID NO:2.

According to certain currently exemplary embodiments, the mALS protein comprises the amino acid sequence set forth in SEQ ID NO:3.

According to certain embodiments, the wild-type SiALS gene comprises a nucleic acid sequence having at least 90% identity to the nucleic acid sequence set forth in SEQ ID NO:2, wherein the sequence comprises an alanine coding sequence at positions 562-564. According to certain embodiments, the wild-type SiALS gene comprises a nucleic acid sequence having at least 95% or more identity to the nucleic acid sequence set forth in SEQ ID NO:2, wherein the sequence comprises an alanine coding sequence at positions 562-564.

According to certain exemplary embodiments, the wild-type SiALS gene comprises the nucleic acid sequence set forth in SEQ ID NO:2.

According to certain embodiments, the alanine-coding sequence comprises the nucleic acids 562-564 of SEQ ID NO:2.

According to certain embodiments, the mALS polynucleotide comprises a substituted codon coding for an amino acid other than alanine at positions 562-564 of a nucleic acid sequence having at least 90% identity to the nucleic acid sequence set forth in SEQ ID NO:2.

According to certain embodiments, the substituted codon codes for the amino acid valine. According to these embodiments, the mALS polynucleotide comprises the nucleotide thymine (T) in position 563 of a nucleic acid sequence having at least 90% identity to the nucleic acid sequence set forth in SEQ ID NO:2.

According to certain currently exemplary embodiments, the mALS polynucleotide comprises the nucleic acid sequence set forth in SEQ ID NO:4.

According to certain embodiments, the mutant polynucleotide encoding the mutant acetolactate synthase is a mutant of the sesame plant endogenous ALS-encoding gene (mSiALS).

According to certain embodiments, the mutant polynucleotide encoding the mutant acetolactate synthase is an exogenous polynucleotide. The Exogenous polynucleotide can be a mutated endogenous ALS gene or a heterologous ALS gene encoding the mutated ALS protein (mALS).

According to certain embodiments, the plant or the part thereof is homozygous to the mALS polynucleotide.

According to certain embodiments, the plant or the part thereof is heterozygous to the mALS polynucleotide.

It is to be explicitly understood that while sesame plants homozygous for the mutant gene encoding the mutant ALS protein having reduced affinity to ALS-inhibiting herbicides exhibit higher tolerance, typically resistance, to ALS-inhibiting herbicides compared to heterozygous plants, the heterozygous plants show significantly enhanced tolerance/resistance compared to plants comprising the wild-type SiALS gene.

According to certain embodiments, the sesame plants of the invention are resistant to ALS-inhibiting herbicides irrespective to the timing of applying the herbicide to the plant, part thereof or to said plant habitat. Timing of herbicide application includes pre-emergence of sesame plants (after sowing before the seedling emerges); post-emergence at the first pair of two true leaves stage; and any time thereafter until plant maturity.

It is to be explicitly understood that the plants resistant to ALS-inhibiting herbicides according to the teachings of the invention are fertile.

According to certain embodiments, the mALS gene and/or the mALS protein have essentially no deleterious effects on the growth rate and pattern of the sesame plant when grown under standard sesame growth conditions.

According to certain exemplary embodiments, the plant resistant to at least one ALS-inhibiting herbicide produces a higher seed yield after being exposed to treatment with the ALS-inhibiting herbicide post-emergence, compared to the yield obtained when the plant is grown under weed-free conditions obtained by alternative weed control methods (i.e., manual weeding).

According to certain embodiments, the ALS-inhibiting herbicide is of a type selected from the group consisting of herbicidal effective Imidazolinones (IMI), Sulfonylureas (SU), Pyrimidinylthiobenzoates (PTB), Triazolopyrimidines (TP), and Sulfonylaminocarbonyltriazolinone (SCT).

According to certain embodiments, the Imidazolinone herbicide is selected from the group consisting of 5-(methoxymethyl)-2-(4-methyl-5-oxo-4-propan-2-yl-1H-imidazol-2-yl) pyridine-3-carboxylic acid (Imazamox); 5-methyl-2-(4-methyl-5-oxo-4-propan-2-yl-1H-imidazol-2-yl) pyridine-3-carboxylic acid (Imazapic); 5-ethyl-2-(4-methyl-5-oxo-4-propan-2-yl-1H-imidazol-2-yl) pyridine-3-carboxylic acid (Imazethapyr); 2-(4-methyl-5-oxo-4-propan-2-yl-1H-imidazol-2-yl)pyridine-3-carboxylic acid (Imazapyr); 4-methyl-2-(4-methyl-5-oxo-4-propan-2-yl-1H-imidazol-2-yl)benzoic acid (Imazamethabenz); methyl 4-methyl-2-(4-methyl-5-oxo-4-propan-2-yl-1H-imidazol-2-yl)benzoate (Imazamethabenz methyl); 2-(4-methyl-5-oxo-4-propan-2-yl-1H-imidazol-2-yl)quinoline-3-carboxylic acid (Imazaquin) and 1-(2-chloroimidazo[1,2-a]pyridin-3-yl)sulfonyl-3-(4,6-dimethoxypyrimidin-2-yl)urea (Imazosulfuron). Each possibility represents a separate embodiment of the present invention.

According to certain embodiments, the Sulfonylurea herbicide is selected from the group consisting of 2-[(4,6-dimethoxypyrimidin-2-yl)carbamoylsulfamoyl]-4-formamido-N,N-dimethylbenzamide (foramsulfuron) and 1-(4,6-dimethoxypyrimidin-2-yl)-3-[3-(2,2,2-trifluoroethoxy) pyridin-2-yl]sulfonylurea (trifloxysulfuron). Each possibility represents a separate embodiment of the present invention.

According to certain embodiments, the Pyrimidinylthiobenzoate herbicide is selected from the group consisting of N-(2,6-difluorophenyl)-8-fluoro-5-methoxy-[1,2,4]triazolo [1,5-c]pyrimidine-2-sulfonamide (Florasulam) and sodium; 2-chloro-6-(4,6-dimethoxypyrimidin-2-yl)sulfanylbenzoate (Pyrithiobac sodium). Each possibility represents a separate embodiment of the present invention.

According to certain embodiments, the Sulfonylaminocarbonyltriazolinone is methyl 2-[(4-methyl-5-oxo-3-propoxy-1,2,4-triazole-1-carbonyl)sulfamoyl]benzoate (Propoxycarbazone).

It is to be explicitly understood that the plants of the invention may be resistant to a single or a plurality of ALS-inhibiting herbicide types. According to certain exemplary embodiments, the plants of the invention are resistant to a plurality of ALS-inhibiting herbicide types, including pre-emergent ALS-inhibiting herbicides and post-emergent ALS-inhibiting herbicides.

According to certain embodiments, the plant part is selected from the group consisting of seeds, pollen, ovules, leaves, embryos, roots, root tips, anthers, flowers, fruit, stems, and shoots. Each possibility represents a separate embodiment of the present invention. Cells and tissue cultures derived from the plant or part thereof are also encompassed within the present invention.

According to certain embodiments, the sesame plant of the invention, characterized as being resistant to at least one ALS-inhibiting herbicide is further characterized by indehiscent capsules.

According to certain embodiments, the sesame plant of the invention is non-transgenic plant.

According to certain embodiments, the non-transgenic plant is produced by creating a mutation within said plant acetolactate synthase encoding gene by cite-directed mutagenesis. According to certain embodiments cite directed mutagenesis is performed by a gene-editing method using at least one artificially engineered nuclease. According to some embodiments, the endonuclease is selected from the group consisting of caspase 9 (Cas9), Cpf1, zinc-finger nucleases (ZFNs), and transcription activator-like effector nucleases (TALENs). According to certain embodiments, the mutation is inserted using CRISPR/Cas system, CRISPR/Cas homologous system or a modified CRISPR/Cas system.

According to other embodiments, the sesame plant of the invention is a transgenic plant comprising at least one cell comprising at least one exogenous polynucleotide encoding an mALS protein having a reduced affinity to at least one ALS-inhibiting herbicide compared to a wild-type SiALS.

The mALS protein having a reduced affinity to at least one ALS-inhibiting herbicide and the polynucleotides encoding same are as described hereinabove.

According to certain exemplary embodiments, the present invention provides a seed of the sesame plants of the invention, wherein a sesame plant grown from the seed comprises at least one cell comprising a mutant acetolactate synthase encoding gene (mALS), wherein the mSAL encodes a mutant acetolactate synthase (mALS) protein having a reduced affinity to at least one ALS-inhibiting herbicide compared to a wild-type *S. indicum* ALS (SiALS) protein, and wherein the plant is resistant to at least one ALS-inhibiting herbicide.

According to additional certain aspects, the present invention provides a method for producing a sesame plant having tolerance and/or resistance to at least one ALS-inhibiting herbicide, the method comprising introducing at least one mutation in at least one allele of the plant endogenous ALS encoding gene, wherein the at least one mutation results in an encoded ALS protein having a reduced affinity to at least one ALS-inhibiting herbicide compared to an ALS protein encoded by a non-mutated gene.

The wild type and mutant proteins and polynucleotides encoding same, and the ALS-inhibiting herbicide are as described hereinabove.

According to further aspects, the present invention provides an isolated polynucleotide encoding acetolactate synthase (ALS) protein having a reduced affinity to at least one ALS-inhibiting herbicide compared to a wild-type *S. indicum* ALS protein.

According to certain embodiments, the encoded ALS protein comprises an amino acid other than alanine at position 188 of a protein having at least 90% identity to the amino acid sequence set forth in SEQ ID NO:1.

According to certain embodiments, the encoded ALS protein comprises an amino acid other than alanine at position 188 of a protein having at least 95% identity to the amino acid sequence set forth in SEQ ID NO:1.

According to certain exemplary embodiments, the encoded protein comprises the amino acid valine at position 188.

According to certain currently exemplary embodiments, the encoded protein comprises the amino acid sequence set forth in SEQ ID NO:3.

According to certain embodiments, the isolated polynucleotide comprises a substituted codon coding for an amino acid other than alanine at positions 562-564 of a nucleic acid sequence having at least 90% identity to the nucleic acid sequence set forth in SEQ ID NO:2.

According to certain embodiments, the isolated polynucleotide comprises a substituted codon coding for an amino acid other than alanine at positions 562-564 of a nucleic acid sequence having at least 95% identity to the nucleic acid sequence set forth in SEQ ID NO:2.

According to certain exemplary embodiments, the isolated polynucleotide comprises a valine-encoding codon at positions 562-564. According to certain currently exemplary embodiments, the isolated polynucleotide comprises the nucleotide thymine (T) in position 563 of a nucleic acid sequence having at least 90% identity to the nucleic acid sequence set forth in SEQ ID NO:2.

According to further currently exemplary embodiments, the isolated polynucleotide comprises the nucleotide thymine (T) in position 563 of SEQ ID NO:2 to form SEQ ID NO:4.

According to certain embodiments, the isolated polynucleotide is comprised within a DNA construct further comprising at least one regulatory element. According to certain embodiments, the regulatory element is selected from the group consisting of a promoter, an enhancer, a termination sequence and any combination thereof. According to certain embodiments, the isolated polynucleotide or the DNA construct comprising same is comprised within a plant-cell compatible expression vector.

A host sesame plant cell comprising the isolated polynucleotides of the invention, a DNA construct and/or expression vector comprising same are also encompassed within the scope of the present invention, as well as a sesame plant comprising the host cell.

According to yet additional aspects, the present invention provides a method for identifying a sesame plant having an enhanced tolerance and/or resistance to at least one type of ALS-inhibiting herbicide, the method comprising detecting, in a genetic material obtained from the plant the presence of a nucleic acid marker amplified by a pair of primer comprising the nucleic acid sequence set forth in ID NO:5 (CAGGTTCCCCGTCGTATG) and SEQ ID NO:6 (TCCTTGACAACCCGAGGA).

According to certain embodiments, the amplified marker comprises the nucleic acid sequence set for the in SEQ ID NO:7 (ATCGGCACTGATGTTTTCCAAGAAACCCCT-ATTGTTGAGGTAACTAGGTCG ATTACCAAGCAT-AATTATCTTGTTTTAGATGTTGAGGATAT).

According to certain aspects, the present invention provides a method for producing a sesame plant having tolerance and/or resistance to at least one ALS-inhibiting herbicide, the method comprising introducing into at least one cell of a sesame plant susceptible to ALS-inhibiting herbicide at least one polynucleotide encoding ALS protein having a reduced affinity to at least one ALS-inhibiting herbicide.

According to certain embodiments, the ALS protein having a reduced affinity to at least one ALS-inhibiting herbicide comprises valine at position 188 compared to alanine in a wild-type SiALS protein.

The ALS protein having a reduced affinity to at least one ALS-inhibiting herbicide and the isolated polynucleotide encoding same are as described hereinabove.

According to yet further certain aspects, the present invention provides a method for controlling weeds in the vicinity of at least one sesame plant resistant to at least one ALS-inhibiting herbicide according to the teachings of the invention, the method comprises applying at least one ALS-inhibiting herbicide to the weeds and the plant in an amount sufficient to inhibit the weed growth.

According to certain embodiments, the amount of the ALS-inhibiting herbicide does not significantly inhibit the growth of the sesame plant resistant to the herbicide.

According to certain embodiments, the amount of the ALS-inhibiting herbicide inhibits the growth of a corresponding sesame plant susceptible to the herbicide.

According to certain embodiment, the amount of the ALS-inhibiting herbicide results in an enhanced seed yield of the sesame plant resistant to the herbicide compared to the yield of a corresponding sesame plant resistant to the herbicide grown in a weed-free environment obtained by an alternative weed control method, wherein the herbicide is applied post-emergence.

It is to be understood that any combination of each of the aspects and the embodiments disclosed herein is explicitly encompassed within the disclosure of the present invention.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE FIGURES

FIG. 1A: Genomic sequence of a segment in the SiALS gene. The point mutation and amino acid substation are marked. FIG. 1B: High-resolution melt (HRM) marker for separation between wild-type (S-416), mutant (SiRM), and hybrid ($F_1$) plants (H). The pick for each genotype (wild-type-right line; mutant-left line and hybrid-middle line) is measured in relative fluorescence units (RFU). FIG. 1C: Representative photo of wild-type (up) and SiRM (down) lines under application of increasing dosage of Imazamox: untreated control (0), 3 (⅛X), 6 (¼X), 12 (½X), 24 (X), 48 (2X), 96 (4X), 96 (8X) and 384 (16X) g a.i. $ha^{-1}$. The recommended dose (X=24 g a.i. $ha^{-1}$) is underlined. FIG. 1D: Shoot dry weight calculated relative to the untreated control. The line curves represent the genotype mean (n=5). Shaded areas indicate the standard error. The resistance index (RI) represents the ratio of the $ED_{50}$ between WT and SiRM.

FIG. 2A-D: Visual characterization of the plants 3, 4, 7, and 11 days after treatment (DAT). FIG. 2E: Longitudinal hourly dynamics of photosynthesis assimilation (A) of WT, $F_1$, and SiRM plants in response to Imazamox application. FIG. 2F: Longitudinal dynamics of canopy coverage (green pixels) throughout the experiment. The solid line curves represent the genotype mean (n=4). Shaded areas indicate the standard error.

FIG. 3A: A representative photo of wild type (WT, S-416), hybrid ($F_1$), and mutant (SiRM) plants under untreated control (UTC) and application of Imazamox (IMA, 48 g a.i. $ha^{-1}$) (IMA) at the end of the experiment (21 days after application). FIG.

3B-3D: Nodes length (B), length to the first flower (C), and shoot dry weight (D) of WT, $F_1$, and SiRM plants under UTC and in response to Imazamox application. Data was obtained 21 days after application.

Figure 4A:
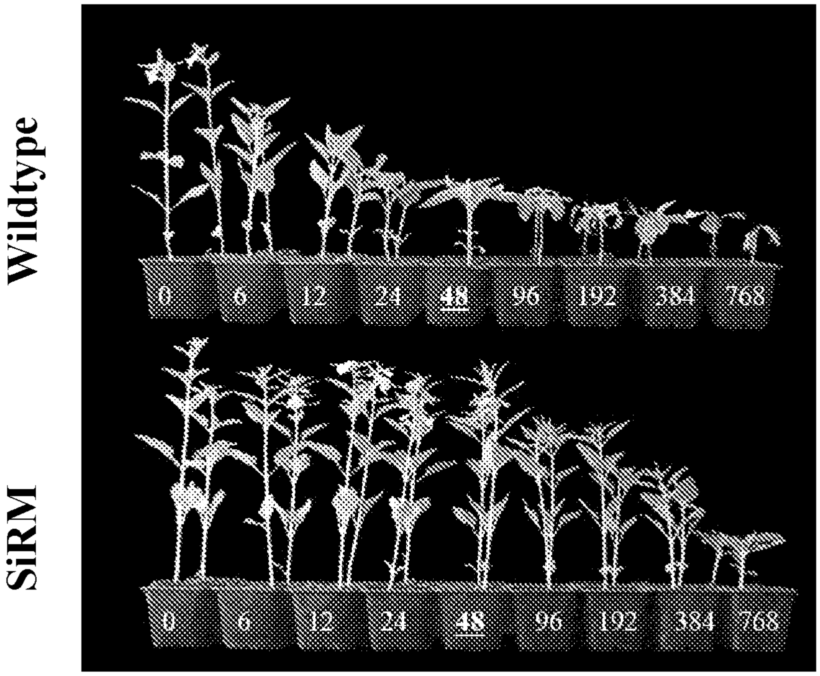
Figure 4B:
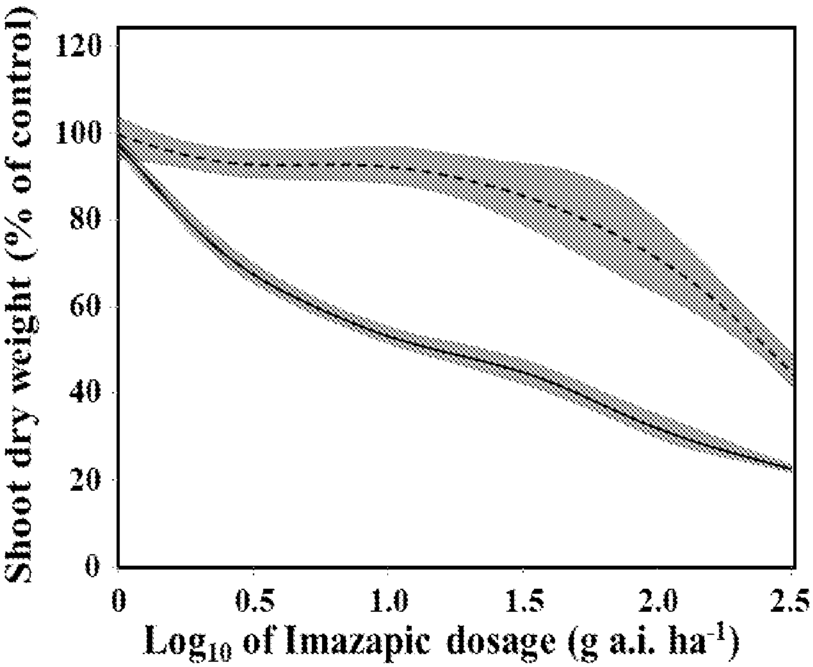
Figure 4C:

FIGS. 4A-4D demonstrate a response to Imazapic and Imazethapyr of wildtype and SiRM plants. FIG. 4A: A representative photo of wild type (S-416, up) and SiRM (down) plants and FIG. 4B: Dose-response to an application of increasing dosage of Imazapic. Untreated control (0), 6 (⅛X), 12 (¼X), 24 (½X), 48 (X), 96 (2X), 192 (4X), 384 (8X) and 768 (16X) g a.i. $ha^{-1}$. The recommended dose (X=48 g a.i. $ha^{-1}$) is underlined. The line curves (dashed: SiRM; solid-WT) represent the genotype mean (n=5). Shaded areas indicate the standard error. FIG. 4C: A representative photo of wild type (S-416, up) and SiRM (down) plants and FIG. 4D: Dose-response to an application of increasing dosage of Imazethapyr. Untreated control (0), 1.25 (⅛X), 2.5 (¼X), 5 (½X), 10 (X), 20 (2X), 40 (4X), 80 (8X) and 160 (16X) g a.i. $ha^{-1}$. The recommended dose (X=10 g a.i. $ha^{-1}$) is underlined. The line curves (dashed: SiRM; solid-WT) represent the genotype mean (n=5). Shaded areas indicate the standard error.

Figure 5B:
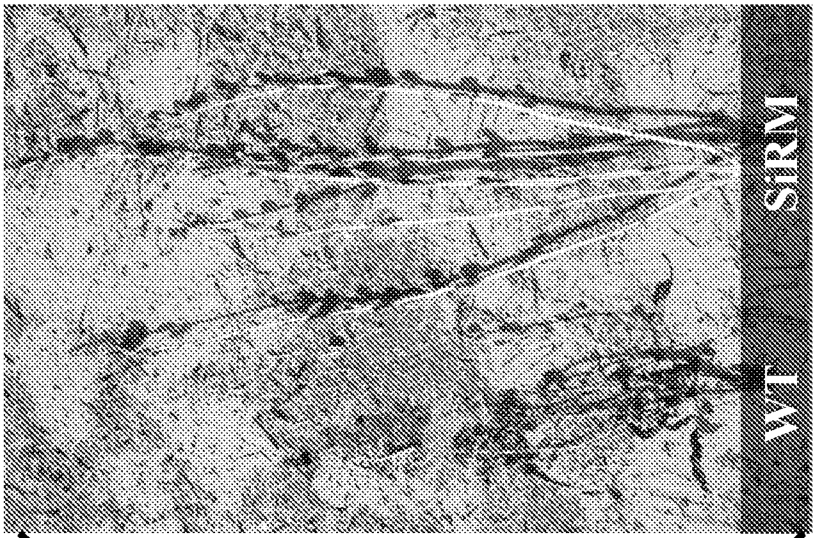
Figure 5A:
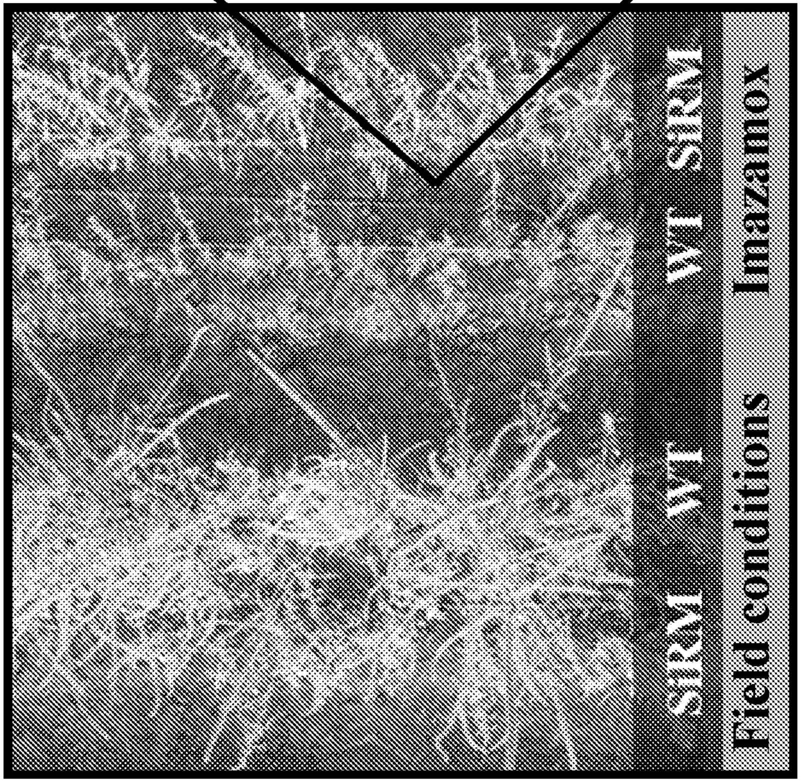
Figure 5D:
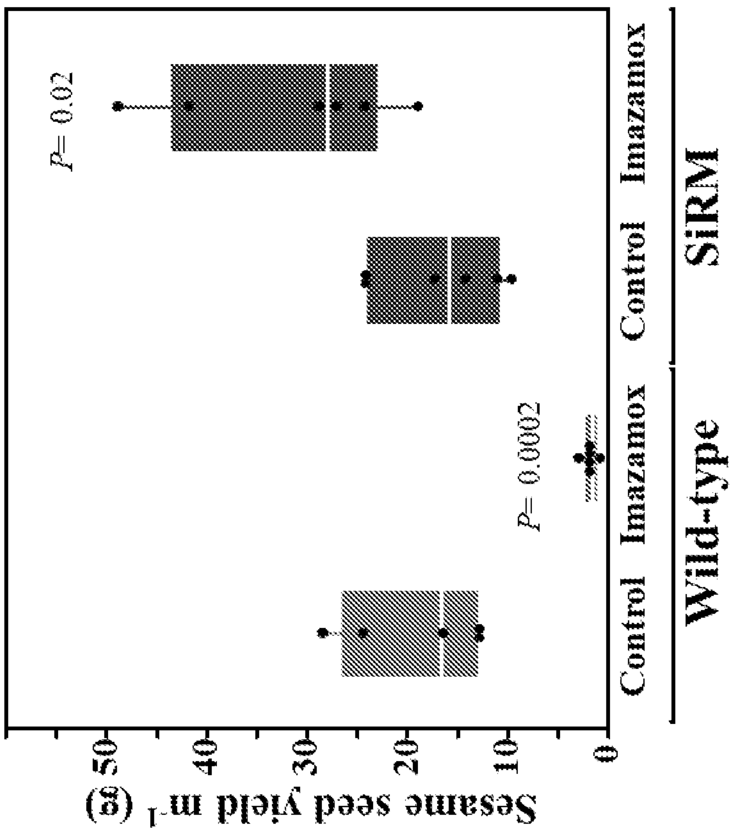
Figure 5C:
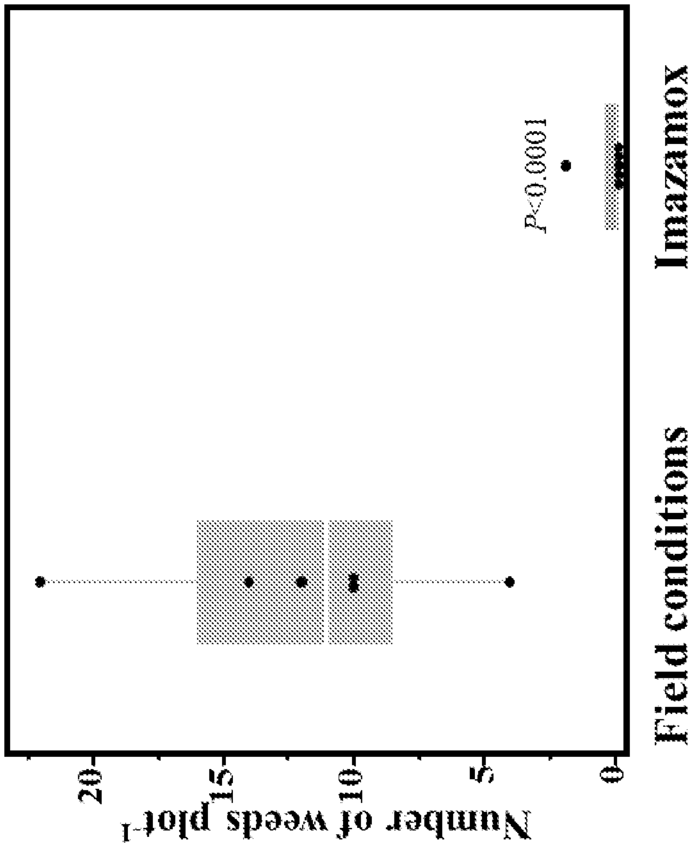
Figure 5E:

FIGS. 5A-5E show the response to Imazamox under field conditions. FIG. 5A: Ariel photo of the plots under field conditions (left, non-treated control *A. palmeri*) and application of Imazamox (right, 40 g a.i. $h^{-1}$). FIG. 5B: A photo of wild type (S-416, WT) and mutant (SiRM) 84 days after application of Imazamox (40 g a.i. $h^{-1}$). FIG. 5C: Quantification of the number of weeds per plot. FIG. 5D: Seed yield at the end of the experiment. FIG. 5E: Arial image observation of WT (S-416; left row) and SiRM (right) plants grown in the field under control (up) and application of Imazapic (48 g a.i. $ha^{-1}$).

Figure 6A:
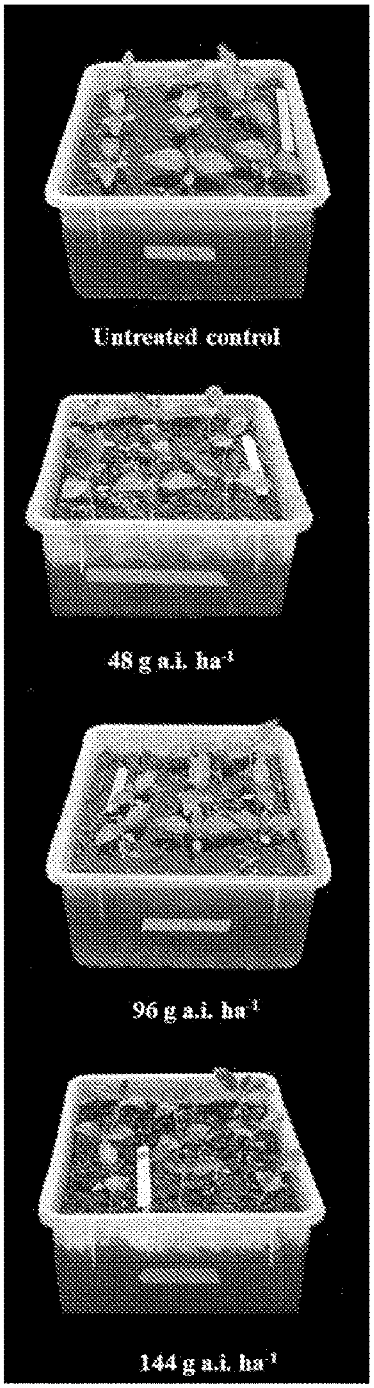
Figure 6B:
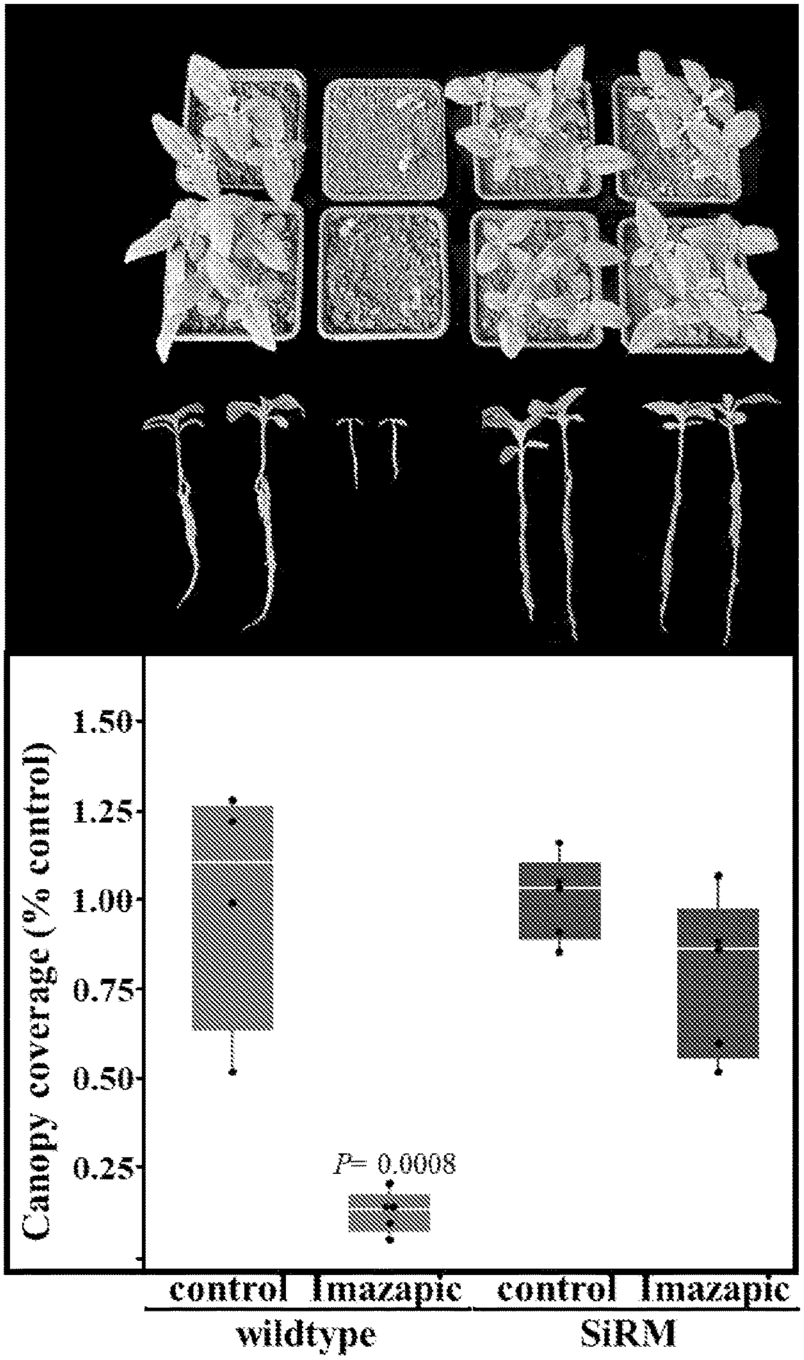
Figure 6C:
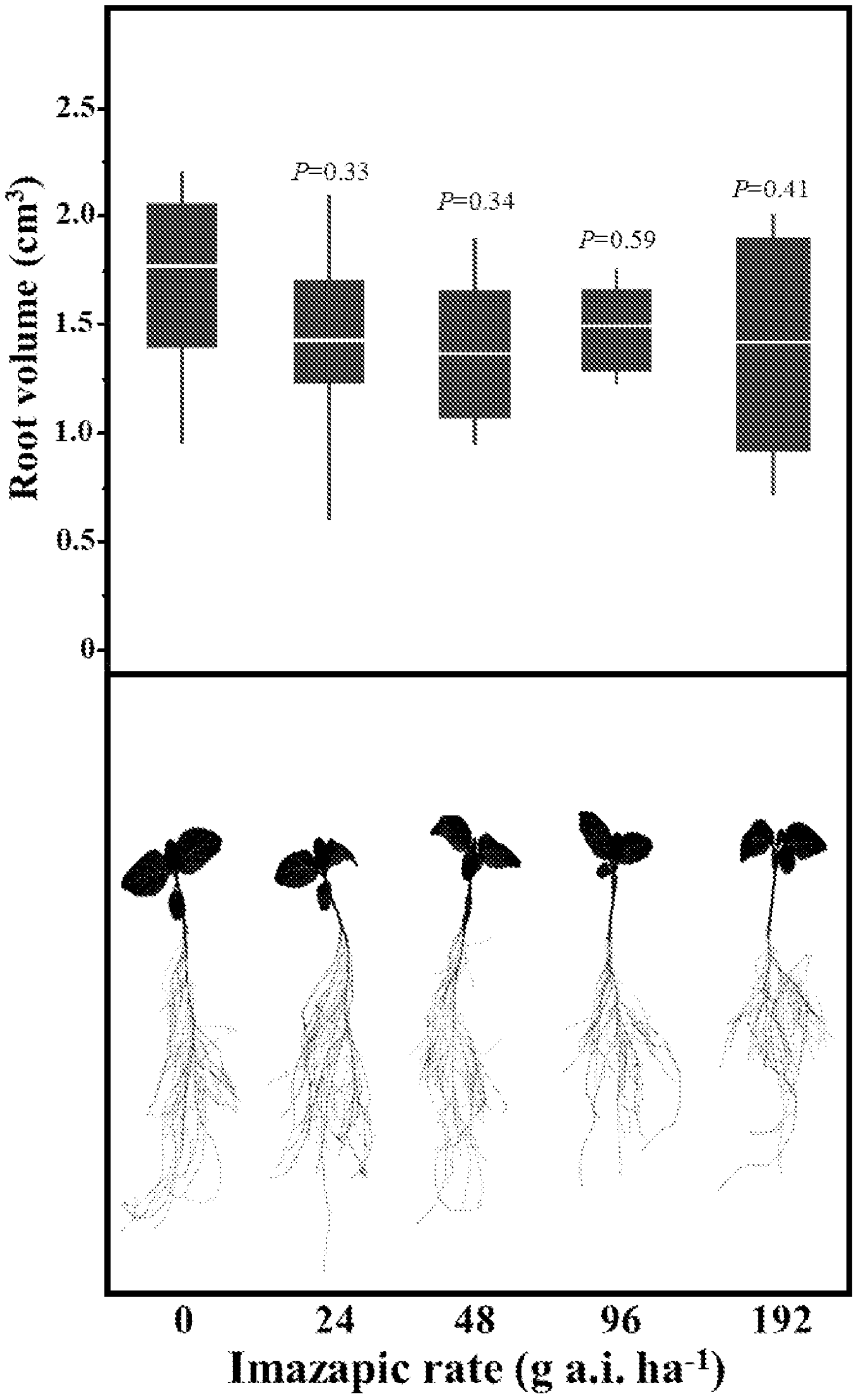

FIGS. 6A-6C show the effect of pre-emergence application of Imazapic on the SiRM plants. FIG. 6A: Dose-response of pre-emergence Imazapic application on SiRM line in clay soil. FIG. 6B: Effect of Imazapic application (144 g a.i. $h^{-1}$) at pre-emergence on wild type (S-416) and mutant (SiRM) plants development and shoot canopy coverage. FIG. 6C: Root volume of SiRM plants in response to an increasing rate of Imazapic.

FIGS. 7A-7E show SiRM response to ALS inhibiting herbicides. FIG. 7A-7E: representative photo of wild type (S-416, up) and SiRM (down) plants and dose-response to an application of increasing dosage of: (A) Trifloxysulfuron (X=12 g a.i. $ha^{-1}$), (B) Foramsulfuron (X=450 g a.i. $ha^{-1}$), (C) Propoxycarbazone (X=48 g a.i. $ha^{-1}$), (D) Florasulam (X=4 g a.i. $ha^{-1}$), and (E) Pyrithiobac sodium (X=68 g a.i. $ha^{-1}$). The recommended dose is underlined. Shoot dry weight calculated relative to the untreated control (UTC). The line curves (dashed line-SiRM; solid line-WT) represent the genotype mean (n=5). Shaded areas indicate the standard error.

Figure 8A:
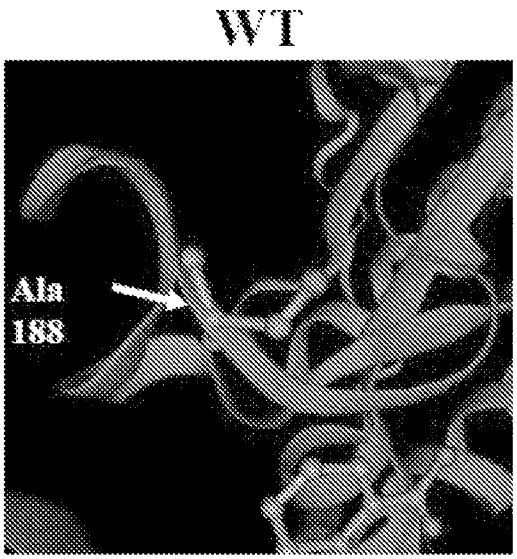
Figure 8C:
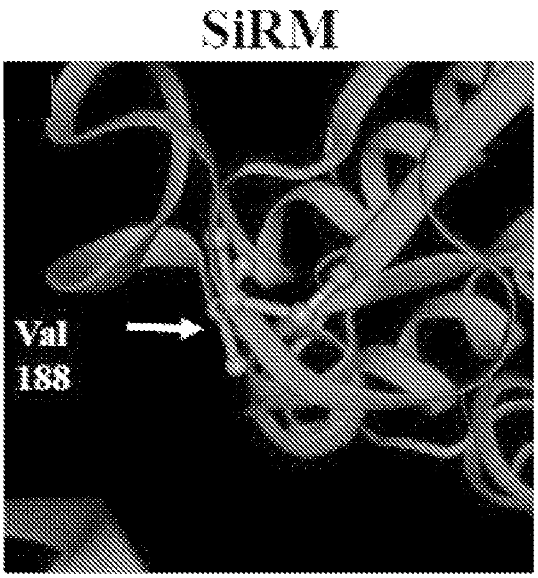
Figure 8B:
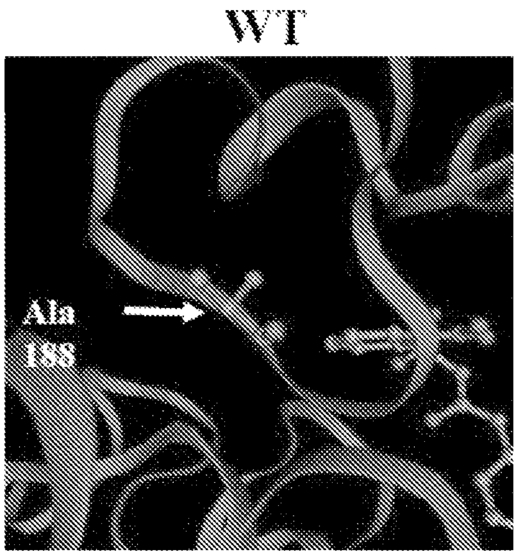
Figure 8D:
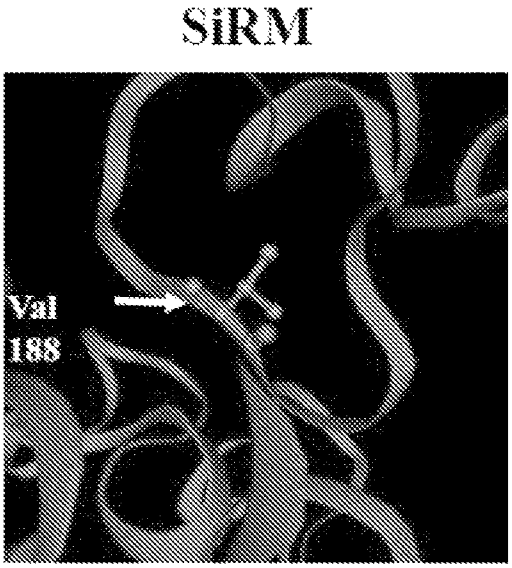

FIGS. 8A-8D show the theoretical protein configuration of a wild type (WT; FIG. 8A-8B) and mutated (SiRM; FIG. 8C-8D) ALS protein.

Figure 9A:
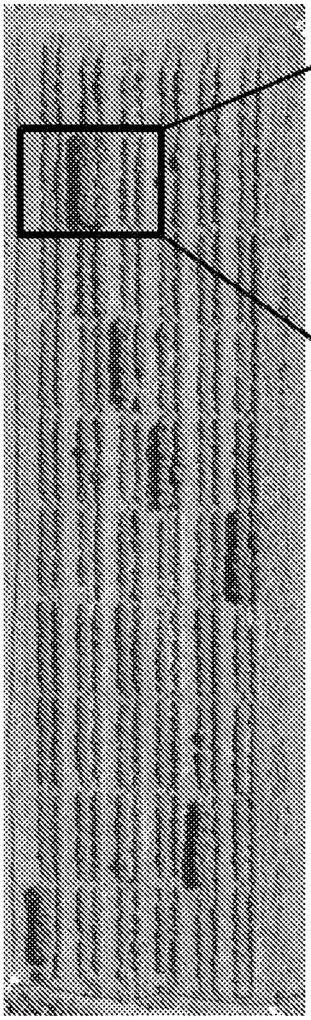
Figure 9B:
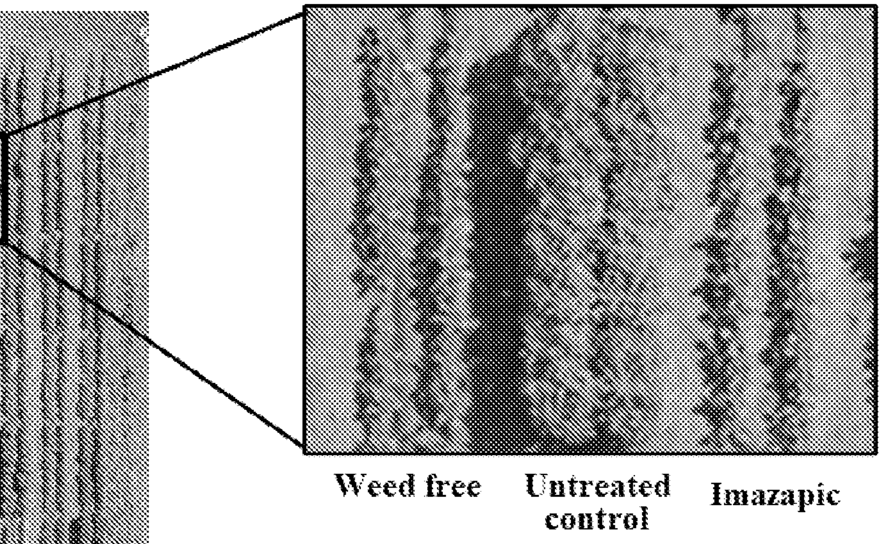
Figure 9C:
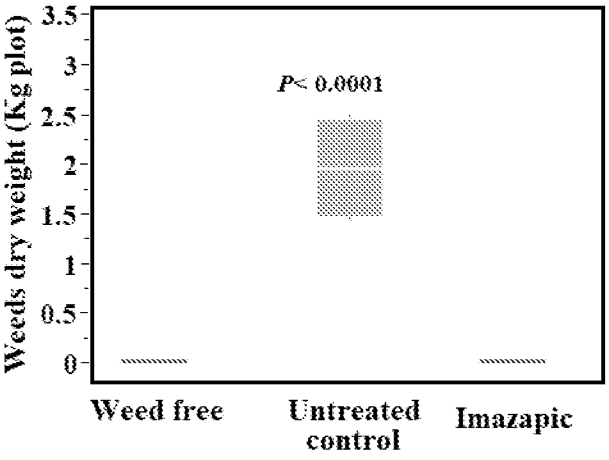

FIGS. 9A-9G show the effect of pre-emergence application of Imazapic on weed control under field conditions. FIG. 9A: Arial photo of the field 25 days after sowing. FIG. 9B: Zoom in on representative plots in the field. FIG. 9C: Total weed dry weight as recorded at the end of the experiment. FIG. 9D: Flowering time, FIG. 9E: Height to the first capsule, FIG. 9F: Number of branches per plant, and FIG. 9G: Seed yield. Box plots represent the mean Box-plots represent the mean (n=6), and the statistical analysis was done by Dunnett' test comparing the treatments to weed-free control.

DETAILED DESCRIPTION OF THE INVENTION

Weeds infestation is a major agronomical factor preventing the implantation of sesame-crop in intensive agrosystems. Thus, developing novel weed-control practices is highly required. The present invention is the first to disclose sesame lines with high tolerance and/or resistance to ALS-inhibiting herbicides. The resistance was obtained by mutation induction and selection of plants resistant to the herbicides. The obtained resistant plant carried a single mutation in the 188 Alanine codon (in relation to the sesame ALS amino acid reference sequence shown in SEQ ID NO:1), which resulted in a change in the ALS protein configuration at the binding site of the herbicide toward decreased affinity of the herbicide to the enzyme. The sesame plants of the invention carrying the mutated ALS were tolerant to broadleaf ALS-inhibiting herbicides applied pre- and post-emergence. The present invention thus significantly contributes to the adoption of integrated weed management in sesame to meet the rising global demand for sesame seeds.

Definitions

The terms "plant" and "sesame plant" are used herein interchangeably in the terms broadest sense. The terms also refer to a plurality of plant cells that are largely differentiated into a structure that is present at any stage of a plant's development. Such structures include, but are not limited to, a root, stem, shoot, leaf, flower, petal, and fruit. According to certain exemplary embodiments, the sesame plants of the present invention are hardy cultivars grown for commercial production of sesame seeds. According to certain exemplary embodiments, the sesame plants of the present invention are indehiscent, i.e., characterized by capsules (fruit) that are visibly closed when fully ripen (matured).

As used herein, the term "plant part" typically refers to a part of the sesame plant. Examples of plant parts include, but are not limited to, pollen, ovules, leaves, embryos, roots, root tips, anthers, flowers, fruit (capsules), stems, shoots, and seeds. The term "plant part" also encompasses single cells and cell tissues such as plant cells that are intact in the plant parts, cell clumps and tissue cultures from which sesame plants can be regenerated.

The terms "Acetolactate synthase", "ALS" ALS protein" and "ALS enzyme" are used herein interchangeably and refer to the enzyme (also known as acetohydroxyacid synthase [AHAS]) involved in the conversion of pyruvate to acetolactate:

$$2CH_3COCO_2^- \rightarrow {}^-O_2CC(OH)(CH_3)COCH_3 + CO_2$$

The reaction uses thiamine pyrophosphate in order to link the two pyruvate molecules. The resulting product of this reaction, acetolactate, eventually becomes valine, leucine, and isoleucine. According to certain embodiments, with reference to wild-type SiALS, the term refers to sesame SiALS having the amino acid sequence set forth in SEQ ID NO:1 or an enzyme having at least 90% sequence identity to SEQ ID NO: 1 comprising alanine at position 188.

It is to be explicitly understood that the wild-type sesame SiALS gene or the encoded protein may, may, or may not, comprise mutations, other than the mutation that causes the Ala188 substitution. As used herein, "sequence identity" or "identity" in the context of two polypeptide or nucleic acid sequences includes reference to the residues in the two sequences which are the same when aligned. When the percentage of sequence identity is used in reference to proteins it is recognized that residue positions that are not identical often differ by conservative amino acid substitutions, where amino acid residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Sequences that differ by such conservative substitutions are considered to have "sequence similarity" or "similarity". Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Henikoff S and Henikoff JG. (Amino acid substitution matrices from protein blocks. Proc. Natl. Acad. Sci. U.S.A. 89(22), 10915-9, 1992).

Identity (e.g., percent homology) can be determined using any homology comparison software, including, for example, the BlastN, BlastX or Blastp software of the National Center of Biotechnology Information (NCBI) such as by using default parameters.

According to certain currently exemplary embodiments of the invention, the identity is a global identity, i.e., an identity over the entire amino acid or nucleic acid sequences of the invention and not over portions thereof.

The term "gene" refers to a nucleic acid (e.g., DNA or RNA) sequence that comprises coding sequences necessary for the production of RNA or a polypeptide. A polypeptide can be encoded by a full-length coding sequence or by any part thereof. The term "parts thereof" when used in reference to a gene refers to fragments of that gene. The fragments may range in size from a few nucleotides to the entire gene sequence minus one nucleotide. Thus, "a nucleic acid sequence comprising at least a part of a gene" may comprise fragments of the gene or the entire gene.

The term "gene" also encompasses the coding regions of a structural gene and includes sequences located adjacent to the coding region on both the 5' and 3' ends for a distance of about 1 kb on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences.

The terms "polynucleotide", "polynucleotide sequence", "nucleic acid sequence", and "isolated polynucleotide" are used interchangeably herein. These terms encompass nucleotide sequences and the like. A polynucleotide may be a polymer of RNA or DNA or hybrid thereof, that is single- or double-stranded, linear or branched, and that optionally contains synthetic, non-natural or altered nucleotide bases. The terms also encompass RNA/DNA hybrids.

As used herein, the term "reduced affinity" with regard to the interaction of ALS enzyme and herbicide refers to a reduction of at least 60%, at least 65%, at least 70%, at least 75%, at least 80%, at least 85%, at least 90%, at least 91%, at least 92%, at least 93%, at least 94%, %, at least 95%, at least 96% at least 97%, at least 98%, at least 99%, or more in the mALS enzyme-herbicide interaction compared to a corresponding wild type ALS-herbicide interaction. The reduced mALS-herbicide affinity results in reduced or no inhibition of the mALS activity by the herbicide. According to certain embodiments, the mALS enzyme shows activity in the presence of an ALS-inhibiting herbicide which is at least 60%, at least 65%, at least 70%, at least 75%, at least 80%, at least 85%, at least 90%, at least 91%, at least 92%, at least 93%, at least 94%, %, at least 95%, at least 96% at least 97%, at least 98%, at least 99%, or identical to its activity in the absence of the herbicide. According to certain additional or alternative embodiments, the mALS enzyme shows activity in the presence of an ALS-inhibiting herbicide which is at least 60%, at least 65%, at least 70%, at least 75%, at least 80%, at least 85%, at least 90%, at least 91%, at least 92%, at least 93%, at least 94%, %, at least 95%, at least 96% at least 97%, at least 98%, at least 99%, or identical to the activity of a corresponding wild type ALS enzyme in the absence of the herbicide.

As used herein, the terms "tolerant", "tolerance", "resistant" or "resistance" of a plant with regard to herbicide(s) treatment refers to a plant that survives treatment with the herbicide. The survived tolerant/resistant plant may show no or reduced symptoms caused by the herbicide. In certain embodiments, a plant tolerant and/or resistant to herbicide shows reduced symptoms when challenged with the herbicide compared to a plant susceptible to said herbicide. For example, a plant tolerant and/or resistant to an herbicide, after the herbicide is applied, can exhibit one or more symptoms associated with the herbicide effect (including, e.g., leaf wilt, leaf or vascular yellowing), spike bleaching etc., and yet not exhibit a reduction in yield in comparison to the yield of a corresponding plant to which the herbicide was not applied and grown under the same conditions.

The application of ethyl methanesulfonate (EMS) mutagenesis chemical was proved to be an efficient approach for producing genetic diversity in many crops, such as tomato [*Solanum lycopersicum* (Dor E et al., 2016. Weed Science, 64:348-360)], rapeseed [*Brassica napus* L. (Channaoui et al., 2019. Oilseeds fats Crop Lipids, 26, 35)], sesame (Kouighat et Journal of Crop Improvement. al., 2020. doi.org/10.1080/15427528.2020.1861155) and many more. In the course of the work of the present invention, a large EMS-mutagenized population (~80,000 M1 plants) was developed according to the small genome size of sesame (~370 Mbps) and the G:C content. In *Arabidopsis*, Jander et al. (2003. Plant Physiology, 131:139-146) found that fewer than 50,000 M1 EMS-mutagenized lines are needed to find a mutation in any given G:C base pair in the genome. Likewise, in soybean, Sebastian et al. (1989. Crop Science, 29:1403-1408) found resistance to ALS herbicide using a population of 70,000 M1 plants. Field-based screening of response to Imidazolinone herbicide (IMI), resulted in the identification of a single mutant plant (SiRM).

The genetic analysis exposed a point mutation in the SiALS gene which confers a change in amino acid Ala188.

The SiRM plants exhibited strong resistance to Imazamox, under both controlled (up to 192 g a.i. $ha^{-1}$) and field (48 g a.i. $ha^{-1}$) conditions (FIGS. 1 and 5). Similarly, high resistance was found for other widely used members of the Imidazolinone class, Imazapic and Imazethapyr (FIGS. 4 and 6).

Thus, according to certain aspects, the present invention provides a sesame (*Sesamum indicum* L.) plant or a part thereof comprising at least one cell comprising a mutant acetolactate synthase encoding gene (mALS), wherein the mALS encodes a mutant acetolactate synthase (mALS) protein having a reduced affinity to at least one ALS-inhibiting herbicide compared to a wild-type *S. indicum*

ALS (SiALS) protein, and wherein the plant is resistant to at least one ALS-inhibiting herbicide.

According to certain embodiments, the wild-type SiALS protein comprises an amino acid sequence having at least 91%, least 92%, least 93%, least 94%, least 95%, least 96%, least 97%, least 98%, least 99%, or more identity to the amino acid sequence set forth in SEQ ID NO:1 wherein the amino acid sequence comprises alanine at position 188. Each possibility represents a separate embodiment of the present invention.

According to certain exemplary embodiments, the wild-type SiALS protein comprises the amino acid sequence set forth in SEQ ID NO:1.

According to certain embodiments, the mALS protein comprises an amino acid other than alanine at position 188 of a protein having at least 90%, at least 91%, at least 92%, at least 93%, at least 94%, at least 95%, at least 96%, at least 97%, at least 98%, at least 99% or more identity to the amino acid sequence set forth in SEQ ID NO:1. Each possibility represents a separate embodiment of the present invention.

According to certain currently exemplary embodiments, the alanine is substituted by valine (Ala188Val). According to these embodiments, the mALS protein comprises the amino acid valine at position 188 of an amino acid sequence having at least 90%, at least 91%, at least 92%, at least 93%, at least 94%, at least 95%, at least 96%, at least 97%, at least 98%, at least 99% or more identity to the nucleic acid sequence set forth in SEQ ID NO:2. Each possibility represents a separate embodiment of the present invention.

According to certain currently exemplary embodiments, the mALS protein comprises the amino acid sequence set forth in SEQ ID NO:3.

According to certain embodiments, the wild-type SiALS gene comprises a nucleic acid sequence having at least 90%, at least 91%, at least 92%, at least 93%, at least 94%, at least 95%, at least 96%, at least 97%, at least 98%, at least 99% or more identity to the nucleic acid sequence set forth in SEQ ID NO:2, wherein the sequence comprises an alanine coding sequence at positions 562-564. Each possibility represents a separate embodiment of the present invention.

According to certain exemplary embodiments, the wild-type SiALS gene comprises the nucleic acid sequence set forth in SEQ ID NO:2.

According to certain embodiments, the alanine-coding sequence comprises the nucleic acids 562-564 of SEQ ID NO:2.

According to certain embodiments, the mALS polynucleotide comprises a substituted codon coding for an amino acid other than alanine at positions 562-564 of a nucleic acid sequence having at least 90%, at least 91%, at least 92%, at least 93%, at least 94%, at least 95%, at least 96%, at least 97%, at least 98%, at least 99% or more identity to the nucleic acid sequence set forth in SEQ ID NO:2. Each possibility represents a separate embodiment of the present invention.

According to certain embodiments, the substituted codon codes for the amino acid valine. According to these embodiments, the mALS polynucleotide comprises the nucleotide thymine (T) in position 563 of a nucleic acid sequence having at least 90%, at least 91%, at least 92%, at least 93%, at least 94%, at least 95%, at least 96%, at least 97%, at least 98%, at least 99% or more identity to the nucleic acid sequence set forth in SEQ ID NO:2. Each possibility represents a separate embodiment of the present invention.

According to certain currently exemplary embodiments, the mALS polynucleotide comprises the nucleic acid sequence set forth in SEQ ID NO:4.

Relying the weed control on a single class herbicide is not a recommended agricultural practice, as it can lead to rapid selection pressure and expose resistant weeds (Kumar et al., 2018, International Journal of Chemical Studies, 6:2844-2850). Therefore, to test if the newly identified mutation can promote resistance to the other four classes of ALS inhibitors, representative herbicides of each class were screened. In general, SiRM plants were more resistant to each of the herbicides (i.e., RI>2) tested, as compared to WT plants. Under the application of SU. TP, and SCT representative herbicides, SiRM plants exhibited tolerance at the field dosage while WT plants were susceptible to all classes (FIG. 7; Table 3). The present invention thus allows flexibility in the use of ALS-inhibiting classes of herbicides to control a wider variety of weeds and reduce the risk, to some extent, of the development of resistant weeds.

According to certain embodiments, the ALS-inhibiting herbicide is selected from the group consisting of herbicidal effective Imidazolinones (IMI), Sulfonylureas (SU), Pyrimidinylthiobenzoates (PTB), Triazolopyrimidines (TP), and Sulfonylaminocarbonyltriazolinone (SCT).

As used herein, the term "imidazolinone" means an herbicidal composition comprising one or more chemical compounds of the imidazolinone class, including, but not limited to, 2-(2-imidazolin-2-yl)pyridines, 2-(2-imidazolin-2-yl)quinolines and 2-(2-imidazolin-2-yl) benzoates or derivatives thereof, including their optical isomers, diastereomers and/or tautomers exhibiting herbicidal activity. According to certain embodiments, the Imidazolinone herbicide is selected from the group consisting of 5-(methoxymethyl)-2-(4-methyl-5-oxo-4-propan-2-yl-1H-imidazol-2-yl) pyridine-3-carboxylic acid (Imazamox); 5-methyl-2-(4-methyl-5-oxo-4-propan-2-yl-1H-imidazol-2-yl) pyridine-3-carboxylic acid (Imazapic); 5-ethyl-2-(4-methyl-5-oxo-4-propan-2-yl-1H-imidazol-2-yl) pyridine-3-carboxylic acid (Imazethapyr); 2-(4-methyl-5-oxo-4-propan-2-yl-1H-imidazol-2-yl)pyridine-3-carboxylic acid (Imazapyr); 4-methyl-2-(4-methyl-5-oxo-4-propan-2-yl-1H-imidazol-2-yl)benzoic acid (Imazamethabenz); methyl 4-methyl-2-(4-methyl-5-oxo-4-propan-2-yl-1H-imidazol-2-yl)benzoate (Imazamethabenz methyl); 2-(4-methyl-5-oxo-4-propan-2-yl-1H-imidazol-2-yl)quinoline-3-carboxylic acid (Imazaquin) and 1-(2-chloroimidazo[1,2-a]pyridin-3-yl)sulfonyl-3-(4,6-dimethoxypyrimidin-2-yl)urea (Imazosulfuron). Each possibility represents a separate embodiment of the present invention.

As used herein, the term "sulfonylurea" refers to an herbicidal composition comprising one or more chemical compounds of the sulfonylurea class, which generally comprise a sulfonylurea bridge, —SO2NHCONH—, linking two aromatic or heteroaromatic rings. According to certain embodiments, the Sulfonylurea herbicide is selected from the group consisting of 2-[(4,6-dimethoxypyrimidin-2-yl)carbamoylsulfamoyl]-4-formamido-N,N-dimethylbenzamide (foramsulfuron) and 1-(4,6-dimethoxypyrimidin-2-yl)-3-[3-(2,2,2-trifluoroethoxy)pyridin-2-yl]sulfonylurea (trifloxysulfuron). Each possibility represents a separate embodiment of the present invention.

According to certain embodiments, the Pyrimidinylthiobenzoate herbicide is selected from the group consisting of N-(2,6-difluorophenyl)-8-fluoro-5-methoxy-[1,2,4]triazolo[1,5-c]pyrimidine-2-sulfonamide (Florasulam) and sodium; 2-chloro-6-(4,6-dimethoxypyrimidin-2-yl)sulfanylbenzoate (Pyrithiobac sodium). Each possibility represents a separate embodiment of the present invention.

According to certain embodiments, the Sulfonylaminocarbonyltriazolinone is methyl 2-[(4-methyl-5-oxo-3-propoxy-1,2,4-triazole-1-carbonyl)sulfamoyl]benzoate (Propoxycarbazone).

The genetic inheritance of known resistance to ALS inhibitors was suggested to be controlled by a complete or partial dominant allele (Yu and Powles, 2014. Pest Management Science, 70:1340-1350), and differ between species and dosage of application (Ghanizadeh et al., 2019, ibid). To evaluate the mode of inheritance in sesame the hybrid response to Imazamox (48 g a.i. $ha^{-1}$) and of the parental lines (WT and SiRM) was characterized. An intermediate response for the $F_1$ plants during the first 4 days after application, and full photosynthetic recovery afterward was observed. These results indicate an additive effect in which each copy of the resistant allele promotes a higher level of resistance. Imaizumi et al. (2008. Weed Research, 48:187-196) suggested, based on the allelic test of $F_2$ population for SU-resistant×susceptible *Monochoria vaginalis* plants, that at a low dose (i.e., 25 g a.i. $ha^{-1}$ bensulfuron-methyl) there is a dominant response of the resistance allele and at high dose (i.e., 225 g a.i. $ha^{-1}$) the susceptible allele is dominant. Together, these findings indicate that the number of copies of the mutant ALS enzyme on one hand, and the number of herbicide molecules on the other, play a key role in the level of resistance, and may change between species and environmental conditions.

The present invention now shows that under field conditions, SiRM plants treated, post-emergence, with the ALS-inhibiting herbicide Imazamox, exhibited a two-fold greater yield compared to the corresponding weed-free UTC (FIG. 5D). Without wishing to be bound by any specific theory or mechanism of action this phenomenon may be a consequence of the phloemic mobility of ALS-herbicides, primarily, to the apical meristems (Russell et al., 2002. Pestic Outlook, 13:166-173).

Thus, according to certain embodiments, the plant resistant to at least one ALS-inhibiting herbicide produces a higher seed yield after being exposed to treatment with the ALS-inhibiting herbicide compared to the yield obtained when the plant is grown under conditions of mechanical/manual weed control, wherein said ALS-inhibiting herbicide is applied post-emergence.

During the first two days after application of Imazamox, the mutant plants exhibit a slight yellowing of the apex, which may lead to the breaking of the apical meristem dominance and alters the source-sink relationship. Likewise, it has been shown that sesame cutting of apical bud can increase the formation of lateral branches and increase seed yield (Vasanthan et al., 2019. International Journal of Chemical Studies, 7:4180-4183). Unexpectedly, following the above mention recovery, the hybrid plants exhibited a compact and bushy phenotype (i.e., shorter nodes) (FIG. 3), which further supports the partial break of the apical meristem dominance. Reduced height up to the first flower (=capsule) was observed in the field trial using the pre-emergence ALS-inhibiting herbicide Imazapic (FIG. 9). From an agronomical perspective, such modification in plant architecture can promote earlier development of branches on the first internodes, reducing the risk of lodging, maximizing the yield potential and supporting a mechanical harvest of the mutant plants of the invention. Thus, this phenomenon offers a dual effect to the farmers, not only efficient weed control (FIG. 7) but also improved yield.

According to certain embodiments, the sesame plant of the invention, characterized as being resistant to at least one ALS-inhibiting herbicide is further characterized by indehiscent capsules.

According to certain embodiments, the sesame plant of the invention comprises at least one cell comprising a mutant acetolactate synthase (mALS) gene, encoding a mutant acetolactate synthase (mALS) protein having a reduced affinity to at least one ALS-inhibiting herbicide compared to a wild-type *S. indicum* ALS (SiALS) protein being tolerant and/or resistant to at least one ALS-inhibiting herbicide, further characterized by indehiscent capsules, has the genetic background of *Sesamum indicum* S-91 plant, seeds of which have been deposited with NCIMB Ltd. as the International Depositary Authority under Accession No. 43877.

The ALS-inhibiting herbicide-resistant plants of the present invention can be produced by any method as is known or will be known to a person skilled in the art.

According to certain embodiments, the mutant polynucleotide encoding the mutant acetolactate synthase is a mutant of the sesame plant endogenous ALS-encoding gene (mSiALS).

Any mutation(s) can be inserted into the polynucleotide encoding ALS including deletions, insertions, site-specific mutations including nucleotide substitution and the like, as long as the mutation(s) results in reduced affinity of the encoded protein to an ALS-inhibiting herbicide.

According to certain exemplary embodiments, mutating the endogenous ALS encoding gene of the sesame plant is performed by cite-directed mutagenesis. According to certain embodiments, cite-directed mutagenesis is performed by a gene-editing method.

Genome editing is a reverse genetics method that uses artificially engineered nucleases to cut and create specific double-stranded breaks at a desired location(s) in the genome, which are then repaired by cellular endogenous processes such as, homology directed repair (HDR) and non-homologous end-joining (NFfEJ). NFfEJ directly joins the DNA ends in a double-stranded break, while HDR utilizes a homologous sequence as a template for regenerating the missing DNA sequence at the breakpoint. To introduce specific nucleotide modifications to the genomic DNA, a DNA repair template containing the desired sequence must be present during HDR. Genome editing cannot be performed using traditional restriction endonucleases since most restriction enzymes recognize a few base pairs on the DNA as their target and the probability is very high that the recognized base-pair combination will be found in many locations across the genome resulting in multiple cuts not limited to a desired location. To overcome this challenge and create site-specific single- or double-stranded breaks, several distinct classes of nucleases have been discovered and bioengineered to date. These include the meganucleases, Zinc finger nucleases (ZFNs), transcription-activator like effector nucleases (TALENs) and CRISPR/Cas system.

According to certain embodiments, the plants of the present invention are produced by inserting a mutation within the sesame endogenous ALS gene using the CRISPR/Cas system, a CRISPR/Cas homologous and CRISPR/Cas modified systems.

The CRISPR/Cas system for genome editing contains two distinct components: a gRNA (guide RNA) and an endonuclease e.g., Cas9.

The gRNA is typically a 20-nucleotide sequence encoding a combination of the target homologous sequence (crRNA)

and the endogenous bacterial RNA that links the crRNA to the Cas9 nuclease (tracrRNA) in a single chimeric transcript. The gRNA/Cas9 complex is recruited to the target sequence by the base-pairing between the gRNA sequence and the complement genomic DNA. For successful binding of Cas9, the genomic target sequence must also contain the correct Protospacer Adjacent Motif (PAM) sequence immediately following the target sequence. The binding of the gRNA/Cas9 complex localizes the Cas9 to the genomic target sequence so that the Cas9 can cut both strands of the DNA causing a double-strand break. Comparable with other genome-editing nucleases, Zinc-finger nucleases (ZFNs) and transcription activator-like effector nucleases (TALENs), the double-stranded brakes produced by CRISPR/Cas can undergo homologous recombination or nonhomologous end-joining (NHEJ). The Cas9 nuclease has two functional domains: RuvC and HNH, each cutting a different DNA strand. When both of these domains are active, the Cas9 causes double-strand breaks in the genomic DNA.

Since most genome-editing techniques can leave behind minimal traces of DNA alterations evident in a small number of nucleotides as compared to transgenic plants, crops created through gene editing could avoid the stringent regulation procedures commonly associated with genetically modified (GM) crop development.

According to further aspects, the present invention provides an isolated polynucleotide encoding acetolactate synthase (ALS) protein having a reduced affinity to at least one ALS-inhibiting herbicide compared to a wild-type *S. indicum* ALS protein.

According to certain embodiments, the encoded ALS protein comprises an amino acid other that alanine at position 188 of a protein having at least 90%, at least 91%, at least 92%, at least 93%, at least 94%, at least 95%, at least 96%, at least 97%, at least 98%, at least 99% or more identity to the amino acid sequence set forth in SEQ ID NO:1. According to certain exemplary embodiments, the encoded protein comprises the amino acid valine at position 188.

According to certain currently exemplary embodiments, the encoded protein comprises the amino acid sequence set forth in SEQ ID NO:3.

According to certain embodiments, the isolated polynucleotide comprises a substituted codon coding for an amino acid other than alanine at positions 562-564 of a nucleic acid sequence having at least 90%, at least 91%, at least 92%, at least 93%, at least 94%, at least 95%, at least 96%, at least 97%, at least 98%, at least 99% or more identity to the nucleic acid sequence set forth in SEQ ID NO:2.

According to certain exemplary embodiments, the isolated polynucleotide comprises a valine-encoding codon at positions 562-564. According to certain currently exemplary embodiments, the isolated polynucleotide comprises the nucleotide thymine (T) in position 563 of a nucleic acid sequence having at least 90%, at least 91%, at least 92%, at least 93%, at least 94%, at least 95%, at least 96%, at least 97%, at least 98%, at least 99% or more identity to the nucleic acid sequence set forth in SEQ ID NO:2.

According to further currently exemplary embodiments, the isolated polynucleotide comprises the nucleotide thymine (T) in position 563 of SEQ ID NO:2 to form SEQ ID NO:4.

According to certain embodiments, the isolated polynucleotide is comprised within a DNA construct further comprising at least one regulatory element. According to certain embodiments, the regulatory element is selected from the group consisting of a promoter, an enhancer, a termination sequence and any combination thereof. According to certain embodiments, the isolated polynucleotide or the DNA construct comprising same is comprised within a plant-cell compatible expression vector.

According to certain further aspects, the sesame plants of the invention being tolerant and/or resistant to at least one ALS-inhibiting herbicide are transgenic plants comprising at least one cell comprising at least one exogenous polynucleotide encoding a mutated ALS protein as described hereinabove.

Any method as is known and will be known in the art for introducing an isolated polynucleotide into sesame plant or a part thereof can be used according to the teachings of the present invention.

According to certain embodiments, introducing the isolated polynucleotide into at least one cell of a sesame plant susceptible to ALS-inhibiting herbicide is performed by methods of gene editing as described hereinabove.

According to certain embodiments, introducing the isolated polynucleotide into at least one cell of a sesame plant susceptible to ALS-inhibiting herbicide comprises transforming the at least one cell with said isolated polynucleotide.

As used herein the term “transformation” or “transforming” describes a process by which a foreign nucleic acid sequence, such as a vector, enters and changes a recipient cell into a transformed, genetically modified or transgenic cell. Transformation may be stable, wherein the nucleic acid sequence is integrated into the plant genome and as such represents a stable and inherited trait, or transient, wherein the nucleic acid sequence is expressed by the cell transformed but is not integrated into the genome, and as such represents a transient trait. According to typical embodiments, the nucleic acid sequences of the present invention are stably transformed into a plant cell.

Transforming plants with isolated nucleic acid sequence generally involves the construction of an expression vector that will function in plant cells. According to the teachings of the present invention, such a vector comprises the isolated polynucleotide encoding the nutated ALS protein having reduced affinity to at least one ALS-inhibiting herbicide. Typically, the vector comprises the polynucleotide under control of, or operatively linked to, a regulatory element. According to certain embodiments, the regulatory element is selected from the group consisting of a promoter, enhancer, a translation termination sequence, and any combinations thereof. The vector(s) may be in the form of a plasmid, and can be used, alone or in combination with other plasmids, in a method for producing transgenic ALS-inhibiting herbicide-tolerant and/or resistant sesame plants.

*Agrobacterium*-mediated gene transfer: The *Agrobacterium*-mediated system includes the use of plasmid vectors that contain defined DNA segments which integrate into the plant genomic DNA. Methods of inoculation of the plant tissue vary depending upon the plant species and the *Agrobacterium* delivery system. A widely used approach is the leaf-disc procedure, which can be performed with any tissue explant that provides a good source for initiation of whole-plant differentiation (Horsch et al., 1988. Plant Molecular Biology Manual A5, 1-9, Kluwer Academic Publishers, Dordrecht). A supplementary approach employs the *Agrobacterium* delivery system in combination with vacuum infiltration. *Agrobacterium* mediated transformation protocols for tomato plants are known to a person skilled in the art.

Direct nucleic acid transfer: There are various methods of direct nucleic acid transfer into plant cells. In electroporation, protoplasts are briefly exposed to a strong electric field, opening up mini-pores to allow DNA to enter. In microinjection, the nucleic acid is mechanically injected directly into the cells using micropipettes. In microparticle bombardment, the nucleic acid is adsorbed on microprojectiles such as magnesium sulfate crystals or tungsten particles, and the microprojectiles are physically accelerated into cells or plant tissues. Another method for introducing nucleic acids to plants is via the sonication of target cells. Alternatively, liposome or spheroplast fusion has been used to introduce expression vectors into plants.

Expression vectors can include at least one marker (reporter) gene, operably linked to a regulatory element (such as a promoter) that allows transformed cells containing the marker to be either recovered by negative selection (by inhibiting the growth of cells that do not contain the selectable marker gene), or by positive selection (by screening for the product encoded by the markers gene). Many commonly used selectable marker genes for plant transformation are known in the art, and include, for example, genes that code for enzymes that metabolically detoxify a selective chemical agent which may be an antibiotic or an herbicide, or genes that encode an altered target which is insensitive to the inhibitor. Several positive selection methods are known in the art, such as mannose selection.

Alternatively, the transgenic as well as the non-transgenic sesame plants of the present invention can be identified using a marker specific for the mutant ALS protein.

According to yet additional certain aspects, the present invention provides a method for identifying a sesame plant having an enhanced tolerance and/or resistance to at least one type of ALS-inhibiting herbicide, the method comprising detecting, in a genetic material obtained from the plant, the presence of a nucleic acid marker amplified by a pair of primer comprising the nucleic acid sequence set forth in SEQ ID NO:5 (CAGGTTCCCCGTCGTATG) and SEQ ID NO:6 (TCCTTGACAACCCGAGGA).

According to certain embodiments, the amplified marker comprises the nucleic acid sequence set for the in SEQ ID NO:7. SEQ ID NO:7 comprises the nucleobase thymine (T) at position14.

According to yet further certain aspects, the present invention provides a method for controlling weeds in the vicinity of at least one sesame plant resistant to at least one ALS-inhibiting herbicide according to the teachings of the invention, the method comprises applying at least one ALS-inhibiting herbicide to the weeds and the plant in an amount sufficient to inhibit the weed growth.

According to certain embodiments, the method comprises controlling weeds in a field planted with a plurality of plants resistant to at least one ALS-inhibiting herbicide according to the teachings of the invention. According to these embodiments, the method comprises applying at least one ALS-inhibiting herbicide to the field.

According to certain embodiments, the amount of the ALS-inhibiting herbicide does not significantly inhibit the growth of the sesame plant resistant to the herbicide.

According to certain embodiments, the amount of the ALS-inhibiting herbicide inhibits the growth of a corresponding sesame plant susceptible to the herbicide.

According to certain embodiment, the amount of the ALS-inhibiting herbicide results in an enhanced seed yield of the sesame plant resistant to the herbicide compared to the yield of a corresponding sesame plant resistant to the herbicide grown in a weed-free environment obtained by an alternative weed control method, wherein the herbicide is applied post-emergence.

The following examples are presented in order to more fully illustrate some embodiments of the invention. They should, in no way be construed, however, as limiting the broad scope of the invention. One skilled in the art can readily devise many variations and modifications of the principles disclosed herein without departing from the scope of the invention.

EXAMPLES

Materials and Methods

Development of Mutant Population

The wild-type (WT) sesame line S-416 was selected for the current study. This mechanical harvest adapted line was previously developed by the inventors of the present invention and co-workers for the Mediterranean climate (Sabag et al., 2021. BMC Plant Biology, 21:549). Plants were selfed over six generations to get homozygote uniform seeds. About 80,000 WT seeds were washed and soaked in water for 6 hours. Seeds were divided into five containers with $ddH_2O$ and the mutagen Ethyl methanesulfonate (EMS, Merck KGaA, USA) at a concentration of 0.2, 0.4, 0.6, 0.8, or 1% (v/v). After 16 hours, seeds were washed under running water for 4 hours to remove the remains of the mutagen. $M_1$ seeds were sown in planting trays and transplanted in the field, a month later. At maturation, $M_2$ seeds were harvested as bulk and systematically mixed to randomly distribute the progeny of any given M1 plant.

Screening for Resistant Plants in the Field

The bulk of $M_2$ seeds were sown in the field (Moshav Revaha; 31°38'41.30"N, 34° 45'51.72"E) with clay soil, at a rate of 6,000,000 seeds $ha^{-1}$ (~4.2 million seeds). At the two real leaves stage, plants were sprayed with Imazamox (Pulsar, BSAF, 48 g active ingredient (a.i.) $ha^{-1}$) using a commercial sprayer (Degania Industries Ltd., Israel). To prevent possible plant escape, a second dose after three weeks was applied. A weekly observation was conducted to identify plants that were not affected by the herbicide. The identified candidate plant was harvested for further examination in the laboratory. The *Sesamum indicum* resistant mutant (hereafter SiRM) plant was selfed up to Ms generation.

SiALS Gene Sequencing

Leaf samples (~2 mg) were taken from two-weeks old plants of SiRM M3 plants and the susceptible WT (S-416). Plants were sprayed with Imazamox (48 g a.i. $ha^{-1}$) for resistance validation (after DNA sampling). Genomic DNA was extracted using the CTAB protocol, with modification for sesame as described before (Teboul et al., 2020. Genes, 11, 1221). To test possible mutation(s) in the SiALS gene, a targeted sequencing was applied using four primer pairs covering the whole gene sequence (Table 1) according to the sequenced sesame genome (Zhongzhi No. 13; Wang et al., 2014. Genome Biology, 15:1-13). The gene was amplified, and PCR products were sequenced (HUJI genome center, Israel). Sequence alignment was performed using the Clustal Omega tool (Madeira et al., 2019. Nucleic Acids Research, 47:636-641).

TABLE 1

| List of primers used for sequencing of the sesame SiALS gene segments. | | |
|---|---|---|
| Primer | Sequence (5'-3') | SEQ ID NO. |
| ALS1F | CCCACTCAGCTGCCTCAT | SEQ ID NO: 8 |
| ALS1R | GCGAGGCCAGAGACCAAA | SEQ ID NO: 9 |

TABLE 1-continued

| List of primers used for sequencing of the sesame SiALS gene segments. | | |
|---|---|---|
| Primer | Sequence (5'-3') | SEQ ID NO. |
| ALS2F | AGGGAGGTGTCTTCGCTG | SEQ ID NO: 10 |
| ALS2R | CCTCCAGCTTACCCGTCA | SEQ ID NO: 11 |
| ALS3F | GCTGGGTATGCATGGGAC | SEQ ID NO: 12 |
| ALS3R | TTGTCACACGAGCTGCAG | SEQ ID NO: 13 |
| ALS4F | CAGCACTTGGGTATGGTTGT | SEQ ID NO: 14 |
| ALS4R | TTCGAGTGGGATGTGCC | SEQ ID NO: 15 |

Determination of the Mutant Allelic Configuration

A high-resolution melting (HRM) protocol was developed to determine the allelic configuration of SiALS mutation, based on dsDNA melting temperatures. One μl of forward (CAGGTTCCCCGTCGTATG, SEQ ID NO:5) and reverse (TCCTTGACAACCCGAGGA, SEQ ID NO:6) primers designed to amplify DNA segments that contain the SNP, were mixed with 2 μl of genomic DNA (20 ng/μl), 4 μl of HRM mix (HOT FIREPol EvaGreen HRM Mix, Solis BioDyne, Tartu, Estonia) and 13 μl of $ddH_2O$. Each mix was transferred to a separate well within a plate (96-well Piko PCR Plate, Thermo Fisher Scientific, Massachusetts, USA), and placed in a Real-Time PCR System (PikoReal 96, Thermo Fisher Scientific, Massachusetts, USA). Reaction settings (i.e., cycles, temperature, and duration) were determined according to the supplied protocol.

Herbicides Dose-Response Assays

Seeds of WT and SiRM were sown in a 9×9×10 cm pot with clay soil (57% clay, 23% silt, 20% sand) from Newe Yaar Research Station. At the stage of two true leaves, plants were exposed to increasing rates (0, ⅛X, ¼X, ½X, X, 2X, 4X, 8X) of representative herbicides from all ALS subgroups (Table 2). Herbicides were sprayed on the plants using a Generation 4 Research Track Sprayer (DeVries Manufacturing, Inc., USA) at a 200 L $ha^{-1}$ spray volume. Plant heights were measured sixteen days after treatments (DAT), and the aboveground material was harvested and oven-dried (at 80° C. for 48 h) to obtain the shoot dry weight (DW).

TABLE 2

| List of herbicides used. | | | | |
|---|---|---|---|---|
| Herbicide | Trade name | Chemical family | Manufacturer | Rate range (g a.i. $h^{-1}$ |
| Imazamox | Pulsar | Imidazolinone | BASF Corporation | 3-384 |
| Imazapic | Cadre | Imidazolinone | BASF Corporation | 6-768 |
| Imazethapyr | Pursuit | Imidazolinone | BASF Corporation | 1.25-160 |
| Trifloxysulfuron | Envoke | Sulfonylurea | Syngenta | 1.5-96 |
| Formsulfuron | Equip | Sulfonylurea | Bayer CropScience | 11.25-180 |
| Pyrithiobac-sodium | Staple | Pyrimidinyl-thiobenzoate | Dupont | 8.5-1088 |
| Propoxycarbazone | Olimpus | Sulfonylamino-carbonyltriazolinone | Bayer CropScience | 6-384 |
| Florasulam | Darbuka | Sulfonyd-triazolopyrimidine | Agan-Adama | 0.5-64 |

Physiological Characterization of $F_1$ Hybrid Plants

A cross between SiRM (♂) and the WT (♀) was made to produce $F_1$ seeds. Uniform $F_1$ seeds were sown in a 9×9×10 cm pot with clay soil alongside the two parental lines (WT and SiRM). The pots were placed in a growth chamber under long-day conditions (16/8 light/dark and 32/25° C.). At the stage of two true leaves, half of the plants were sprayed with Imazamox (48 g a.i. $h^{-1}$). Plants were characterized daily for canopy coverage (Canopeo software, Oklahoma State University, USA; Patrignani and Ochsner, 2015. Agronomy Journal, 107:2312-2320) and gas exchange (IRGA 6800; Li-Cor, Lincoln, Nebraska, USA), over the next 11 days. At the end of the experiment, 21 DAT, the aboveground material was harvested, oven-dried (80° C., 48 h), and weighed to obtain shoot DW.

Field Experiments

Imazamox Post-Emergence Experiment

The experiment was conducted in the Experimental Farm of the Hebrew University of Jerusalem in Rehovot, Israel (34°47' N, 31°54' E; 54 m above sea level). The soil at this location is brown-red, degrading, sandy soil (Rhodoxeralf), composed of 76% sand, 8% silt, and 16% clay. A pair-samples experimental design was applied with the two genotypes (WT and SiRM) and two treatments: untreated control (UTC) and Imazamox application (40 g a.i. $h^{-1}$). Each plot consisted of a 5-meter row, with a sowing density of 7-plants $m^{-1}$ (n=6). At the end of the season, the survival rate was analyzed (number of plants per plot) and the plants in the plot were harvested. Samples were threshed using a laboratory thresher (Wintersteiger AG LD 350, Austria) and after sifting, the seeds were weighed to obtain seed yield.

To test the efficiency of Imazamox for weed control, *Amaranthus palmeri* was used as a model. Seeds of *A. palmeri* were sown (20-seeds $m^{-1}$) as competitor weeds alongside the two sesame lines described above. As a negative control, plots that were not treated were used. At the end of the experiment, the number of *A. palmeri* plants per plot was counted.

Imazapic Pre-Emergence Experiment

Seeds of WT and SiRM, and two weed species, *A. palmeri* and *Euphorbia heterophylla* were sowed in pots (9×9×10 cm) with clay soil (Newe Yaar Research Station), 5 seed per pot, except *A. palmeri* with 20 seeds. Five pots from each plant species were sprayed with Imazapic (144 g a.i. $h^{-1}$). Herbicide application was followed by irrigation equivalent to 200-millimeter $ha^{-1}$. The pots were placed in a growth chamber under long-day conditions (16/8 light/dark and 32/25° C.) and the canopy coverage (Canopeo) was measured at 14 DAT.

An additional field experiment was conducted during the summer of 2021 at the Experimental Farm of the Hebrew University of Jerusalem, Rehovot, Israel. A split-plot random block design with six replicates was applied. Treatments included: weed-free plots (i.e., manual weeding), untreated control (i.e., herbicide-free treatment) and application of Imazapic (48 g a.i. $ha^{-1}$) pre-germination. The plot size was 3.6 m×0.8 m (10 cm between plants) with two rows per plot. To evaluate the efficacy of weed control, two weeds were sown on the sesame sowing lines (*Amaranthus Palmeri,* 500 seeds per plot, and *Abutilon* Theophrastus, 70 seeds per plot). Phenological characterization was conducted during the growing season for the flowering date, the number of brunches per plant and the height to the first capsule. At the end of the growing season, the number of weeds per plot was counted and weeds were harvested for dry weight measurements. Sesame plants were harvested 1 m from the middle of the plot, samples were threshed using a laboratory thresher (Wintersteiger AG LD 350, Austria), and after sifting, the seeds were weighed to obtain seed yield.

Characterization of Roots Development Under Increasing Dosages of Imazapic

Three seeds of SiRM were sown in plastic columns (30 cm long) filled with sandy soil (composed of 76% sand, 8% silt, and 16% clay) (n=5) and sprayed with increasing doses of Imazapic (24, 48, 96, and 192 g a.i. $ha^{-1}$). Herbicide application was followed by irrigation equivalent to 200-millimeter $ha^{-1}$ and placed in a growth chamber under long-day conditions (16/8 light/dark and 32/25° C.). Fourteen DAT, the roots were washed and scanned using a flatbed scanner (Epson 12000XL, Seiko EPSON, Japan), and root architecture was analyzed using the WinRHIZO Pro software (Regent Instruments Ltd., Ontario, Canada).

Statistical Analyses

The JMP® (ver. 15) statistical package (SAS Institute Inc., Cary, NC. USA) was used for all statistical analyses. Descriptive statistics are graphically presented in box-plot: median value (horizontal short line), quartile range (25 and 75%), and data range (vertical long line). Dose-response curves were constructed by plotting the shoot DW data 16 DAT, from the different accessions as a percentage of untreated control (UTC). A nonlinear curve model (Exponential two parameters) was adjusted to analyze the effects of the tested herbicides in the different experiments.

$$Y = a \times \text{Exp}\ (b \times d);$$

where Y is the shoot DW, a=scale, b=growth rate, and d represents the herbicide dosage. The resistance/susceptible ratio of the $ED_{50}$ was calculated to determine the resistance index (RI) of the resistant plants compared to that of the susceptible plants.

Figure 1A:
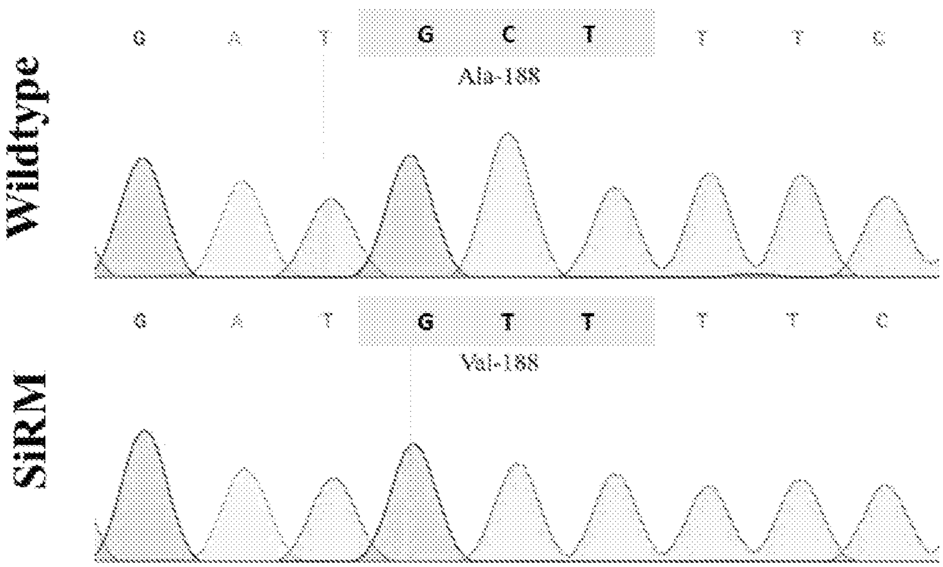
FIGS. 1A-1D demonstrate the identification and validation of point-mutation in the SiALS gene.
Figure 1B:
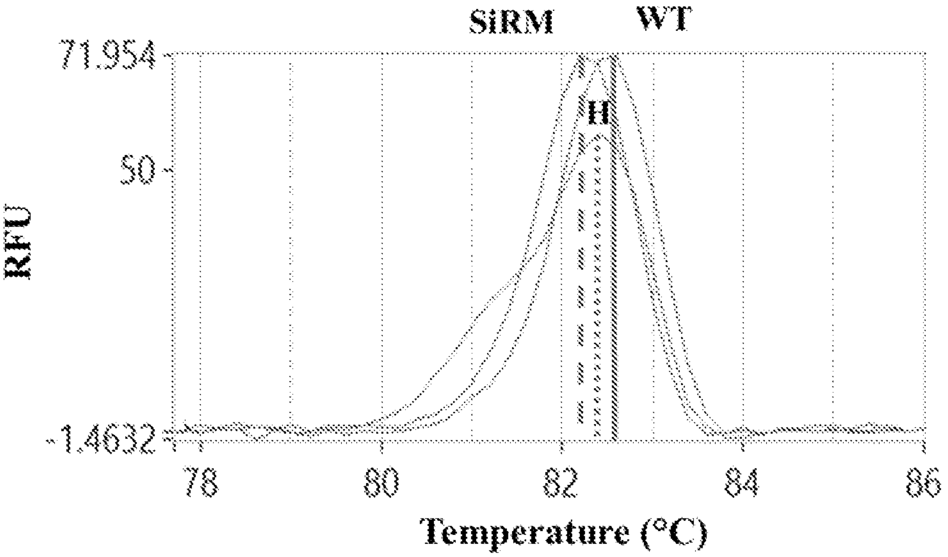
Figure 1C:
Figure 1D:
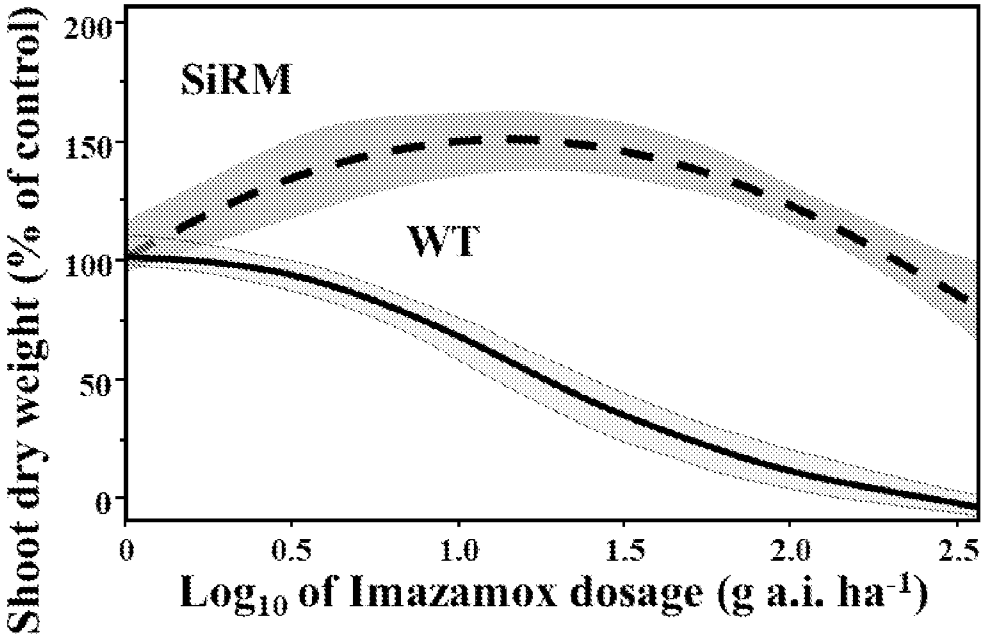

Example 1: Induced Mutation in SiALS Gene Provides High Resistance to Imazamox To identify a possible mutation(s) in the ALS encoding gene, over 4,000,000 M2 plants were screened in the field. Visual characterization of the plants after two consecutive applications of Imazamox (48 g a.i. $ha^{-1}$) resulted in a single candidate plant without any visual symptoms (i.e., no visible growth reduction and meristem damage). Seeds from this candidate plant were harvested, and the M3 plants were sprayed with a similar dose of Imazamox. Seven days after spraying, the WT plants (S-416) showed reduced growth and meristem damages, while the mutant plants (SiRM) did not display any visual symptoms. It is worth noting that SiRM plants exhibited higher vigor under Imazamox treatment as compared with its untreated control (FIG. 1D). To test the possibility of target-site mutation in the SiALS gene, the gene segments were sequenced and a single point mutation in position 563 was identified. This mutation conferred substitution from Cytosine to Thymine (C→T) and amino acid substitution in position 188 in the ALS enzyme from alanine to valine (FIG. 1A). To enable fast screening of this mutation, a high-resolution melt (HRM) marker was developed. This new marker resulted in a clear separation between WT. SiRM, and the $F_1$ hybrid (FIG. 1B). To evaluate the level of resistance, a dose-response assay was conducted, from sub-lethal (3 g a.i. $ha^{-1}$) to 16 times field dosage (i.e., 364 g a.i. $ha^{-1}$). WT plants exhibited visual symptoms and reduced shoot DW already at a low dose of 6 g a.i. $ha^{-1}$ and reached $ED^{50}$ (i.e., reductions of 50% shoot DW) at 18 g a.i. $ha^{-1}$. In contrast, SiRM plants did not show any visual symptoms up to 8× of the recommended dose (192 g a.i. $ha^{-1}$). Consequently, the calculated $ED_{50}$ of the mutant line was at a high rate of 823 g a.i. $ha^{-1}$ (which is above the tested rates) (FIG. 1C-D). Notably, under low doses of 3, 6, and up to half of the recommended field dose 12 g a.i. $h^{-1}$, SiRM plants exhibited a 50% increment in shoot DW as compared with corresponding untreated control plants.

Figure 2A:
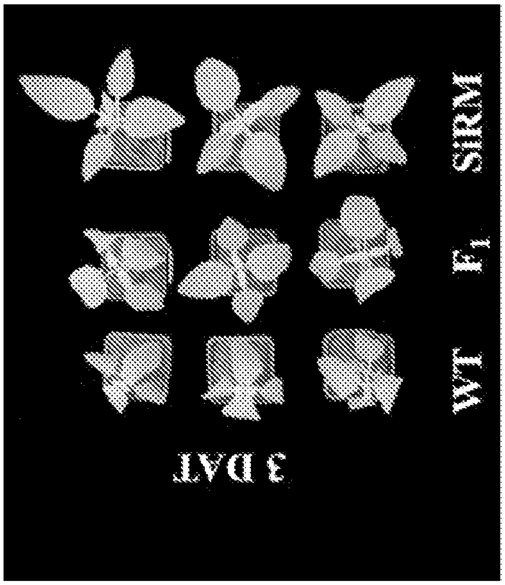
FIGS. 2A-2F demonstrate genetic and physiological characterization of hybrid ($F_1$) plants in response to Imazamox application (48 g a.i. $ha^{-1}$).
Figure 2B:
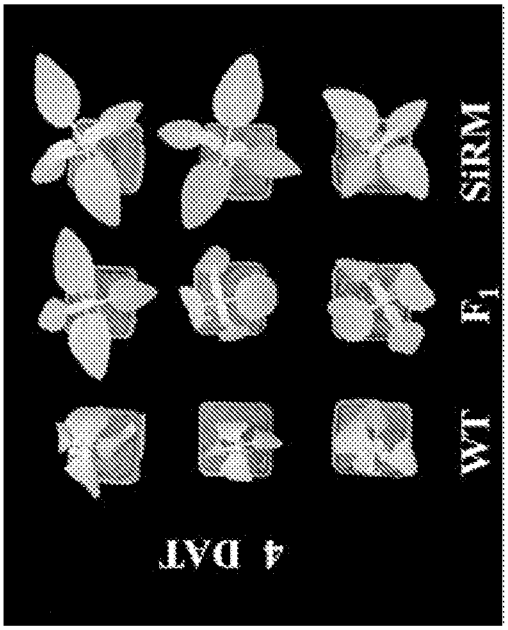
Figure 2C:
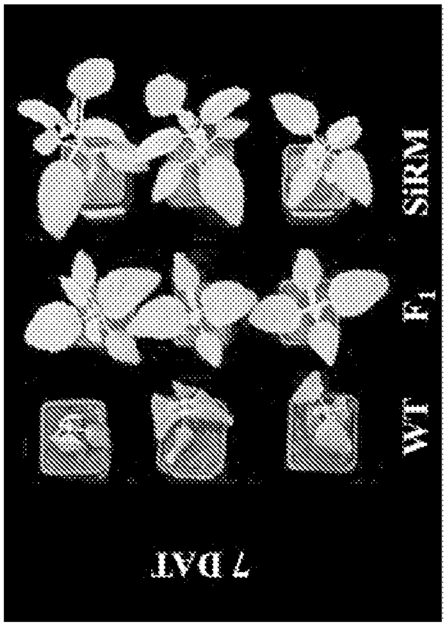
Figure 2D:
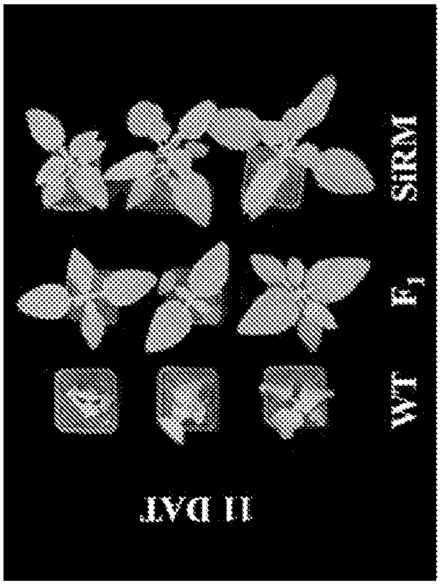
Figure 2E:
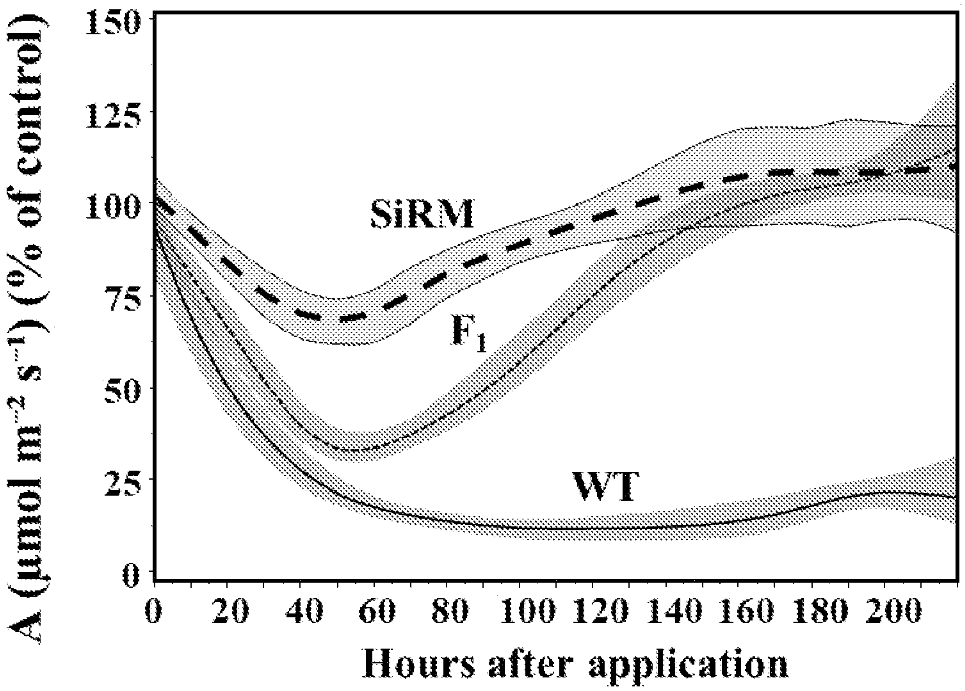
Figure 2F:
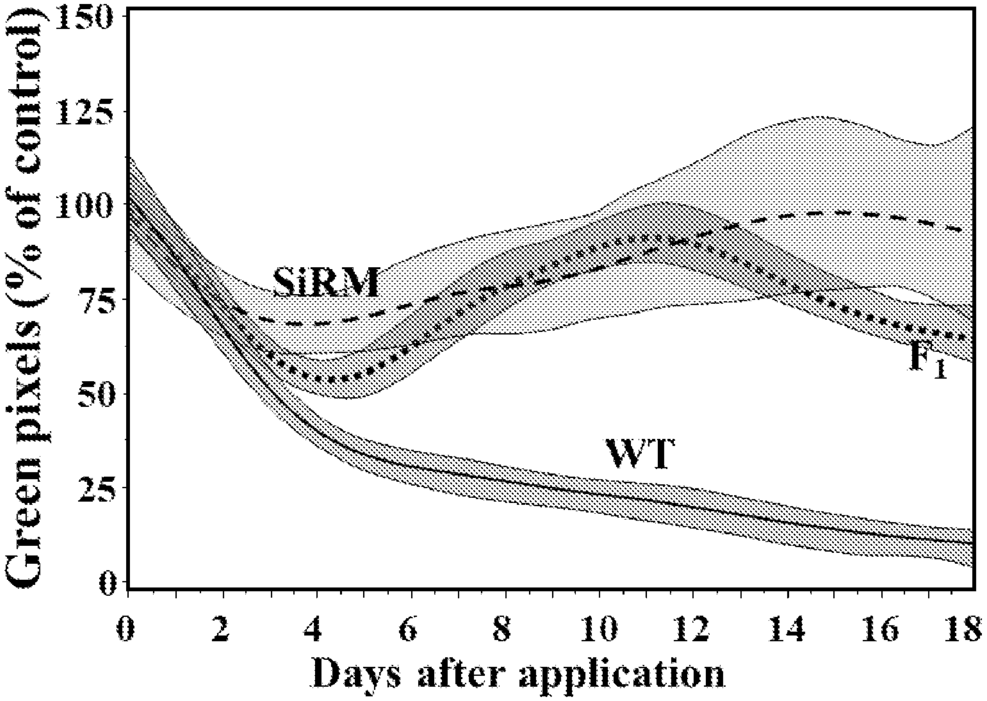
Figure 3A:
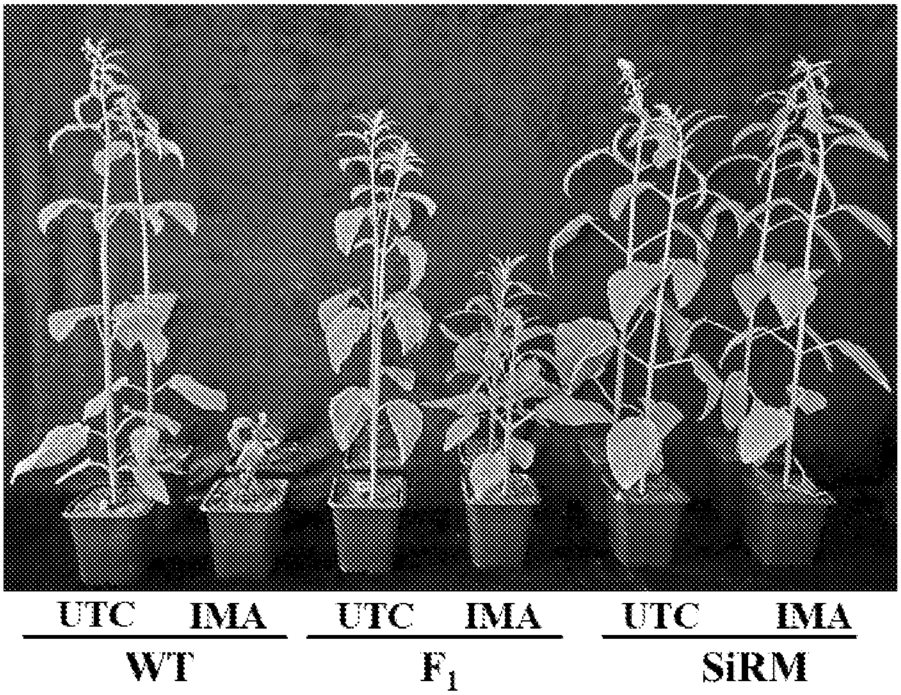
FIGS. 3A-3D demonstrate genetic and physiological characterization of hybrid ($F_1$) plants in response to Imazamox application (48 g a.i. ha-1).
Figure 3B:
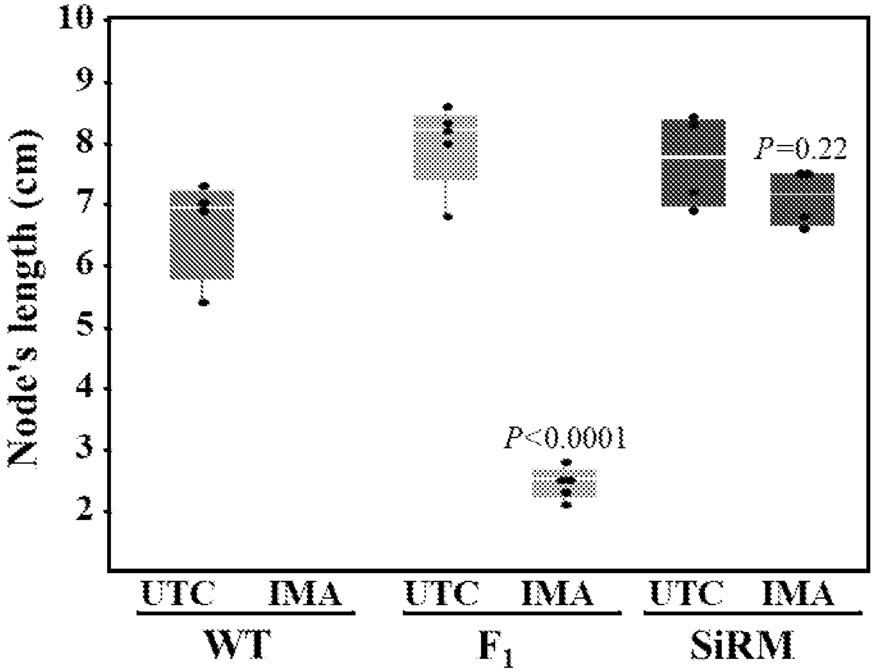
Figure 3C:
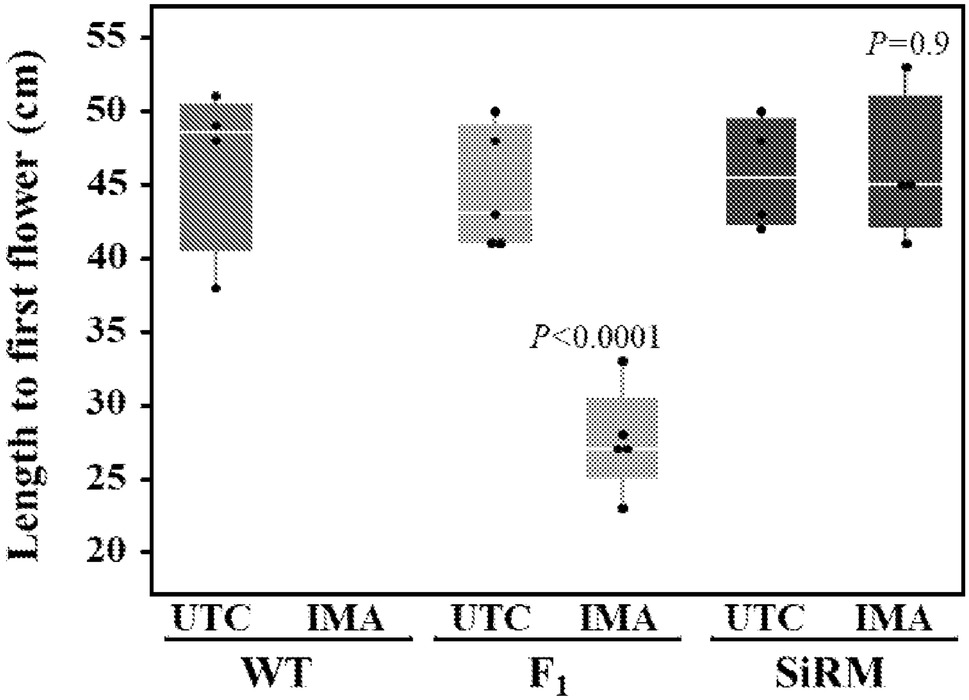
Figure 3D:
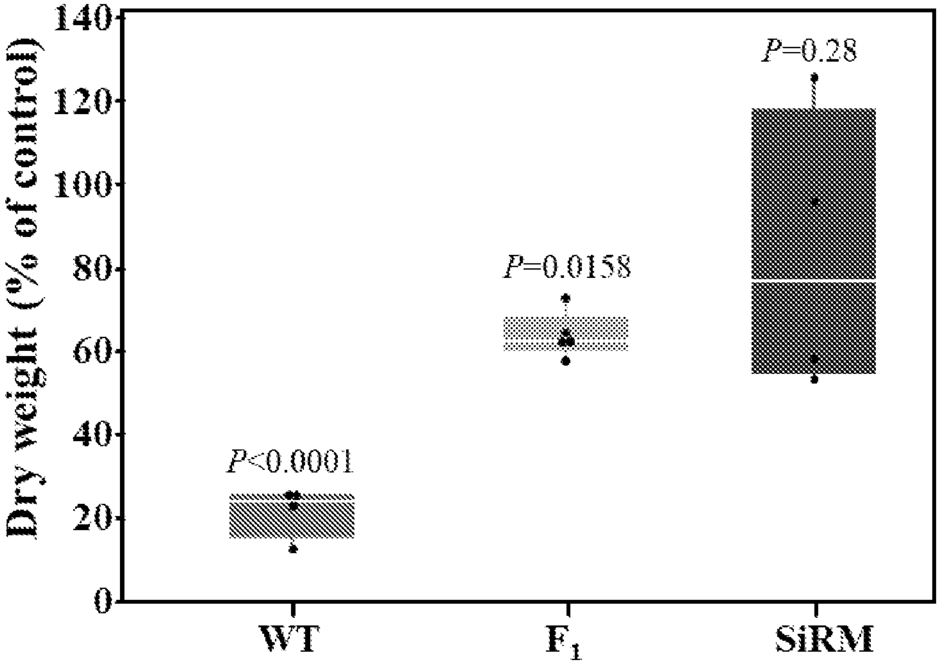

Example 2: Intermediate Response of Hybrid Plants Exhibited Modification in Plant Architecture and Gas Exchange To test the genetic inheritance of the mutant ALS gene the time-response to ALS-inhibitors of hybrid ($F_1$) plants and their parental lines (WT and SiRM) was analyzed. In general, while the SiRM (homozygote) plants did not differ from the UTC plants and maintained a normal growth pattern, both WT and hybrid plants exhibited a significant reduction in growth during the first 4 DAT. The hybrid plants were able to recover and, already after 7 DAT, they looked like the SiRM plants. Fourteen DAT, the hybrid plants shifted their growth pattern from stem elongation to the production of more lateral branch meristems, as expressed in shorter plant height. At the end of the experiment, WT plants were fully eradicated, whereas SiRM plants showed no effect of Imazamox treatment (FIGS. 2F and 3A). The hybrid plants displayed intermediate response as expressed in a reduction of ~40% in plant height, and ~35% in shoot DW (FIG. 3D). Morphological characterization of the hybrid plants showed that the erect morphology was associated with more nodes to the first flower (11.4 vs. 5.6 nodes for treated and UTC, respectively) but shorter nodes (2.4 vs. 8.0 cm), which consequently resulted in lower first flower bud (27.6 vs. 44.6 cm) (FIG. 3B-C).

While all three lines exhibited a similar trend of reduction in assimilation and transpiration during the first 48 hours after application, the severity of response was significantly stronger for the WT plants, with hybrid plants exhibiting intermediate response. After 48 h, WT had less than a 20% assimilation rate, and the SiRM plant recover completely and did not differ from the UTC plants. The hybrid plants showed slower recovery, though after six days they fully recovered (FIG. 2E).

Example 3: Field-Based Validation Confirmed High Resistance and Enhanced Yield To evaluate the level of field resistance and its effectiveness in sesame weed control, a field experiment was done with the two lines (WT and SiRM) under *Amaranthus palmeri* infestation and Imazamox (40 g a.i. $h^{-1}$) application (FIG. 5A). Overall, the Imazamox treatment was very efficient in controlling *A. palmeri* (~0 *A. palmeri* plants per meter plot) compared with the field conditions (non-treated control) (~12 *A. palmeri* plants $m^{-1}$) (FIG. 5C). Application of Imazamox resulted in a significant reduction in WT sesame stand (75%, P<0.0001) due to severe plant death (FIG. 5B). In contrast, there was no significant effect on the SiRM plots stand. At the end of the experiment, the plots were treated with Imazamox, and the weed-free plots (control) were harvested. While the WT plants exhibited significant yield reduction (0.93 vs. 3.6 g per plant for the Imazamox and weed-free control, respectively, P=0.0015), the SiRM plants exhibited the opposite trend. The mutant plants had a double yield per plant under Imazamox treatment compared to plants grown in weed-free plots, where the weeds were eradicated manually (6.05 vs. 2.88 g per plant, respectively, P=0.011). Notably, the differences in plot stand could have affected the obtained results. Therefore, to eliminate this factor, the yield per plot was also analyzed; a similar pattern was obtained at the plot level (FIG. 5D). The WT plots under Imazamox treatment showed significant yield reduction compared to weed-free (control) plots (1.6 vs. 19 g, respectively, P=0.0002). Surprisingly, the mutant plots had a significantly higher yield under Imazamox treatment compared with control (31.5 and 16.7 g, respectively, P=0.02) (FIG. 5D).

Example 4: The Mutation Confers High Resistance to Imidazolinone Herbicide

Figure 4D:
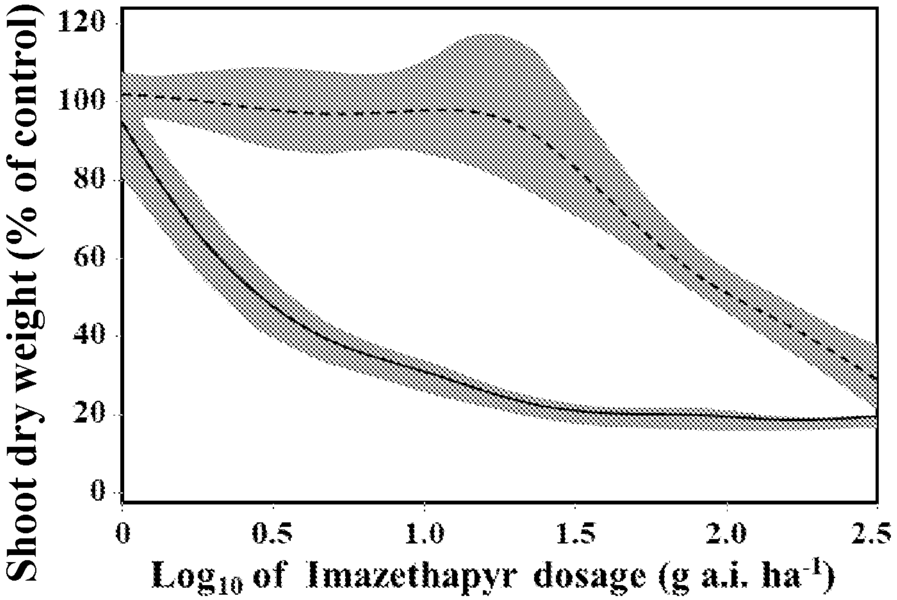

To test if the point mutation in the SiALS gene also promotes resistance to other herbicides in the same class of Imidazolinone, Imazapic and Imazethapyr were used. These herbicides were chosen based on their widespread use in field crops. Dose-response assay showed a similar trend, with clear differences between lines. Under Imazapic application, the WT exhibited a significant reduction in growth already at 6 g a.i. $h^{-1}$ (18%, P=0.0055), which become more pronounced visually as Imazapic dosages increased. SiRM plants were not affected up to 2× of the recommended dose (96 g a.i. $h^{-1}$) and exhibited severe damage symptoms only at a high rate of 16× (768 g a.i. $h^{-1}$; FIG. 4A-B). The same trend was observed after the application of Imazethapyr. All dosages applied on WT plants caused a significant reduction in shoot DW, and the field recommended dosage (20 g a.i. $h^{-1}$) was deadly for the plants. On the other hand, SiRM plants were not affected up to 4× of the recommended dose (80 g a.i. $h^{-1}$), and even at the highest dosage of 160 g a.i. $h^{-1}$ plants were viable and fully recovered (FIG. 4C-D). Field observation of WT vs. SiRM followed Imazapic recommended dose (48 g a.i. $h^{-1}$) application resulted in clear differences. While all WT plants (and weeds) were dead already 10 DAT, the SiRM plants were only slightly affected and showed a five-day delay in shoot development and flowering time.

Example 5: SiRM Exhibited Mild Resistance to Different ALS Classes

Figure 7A:
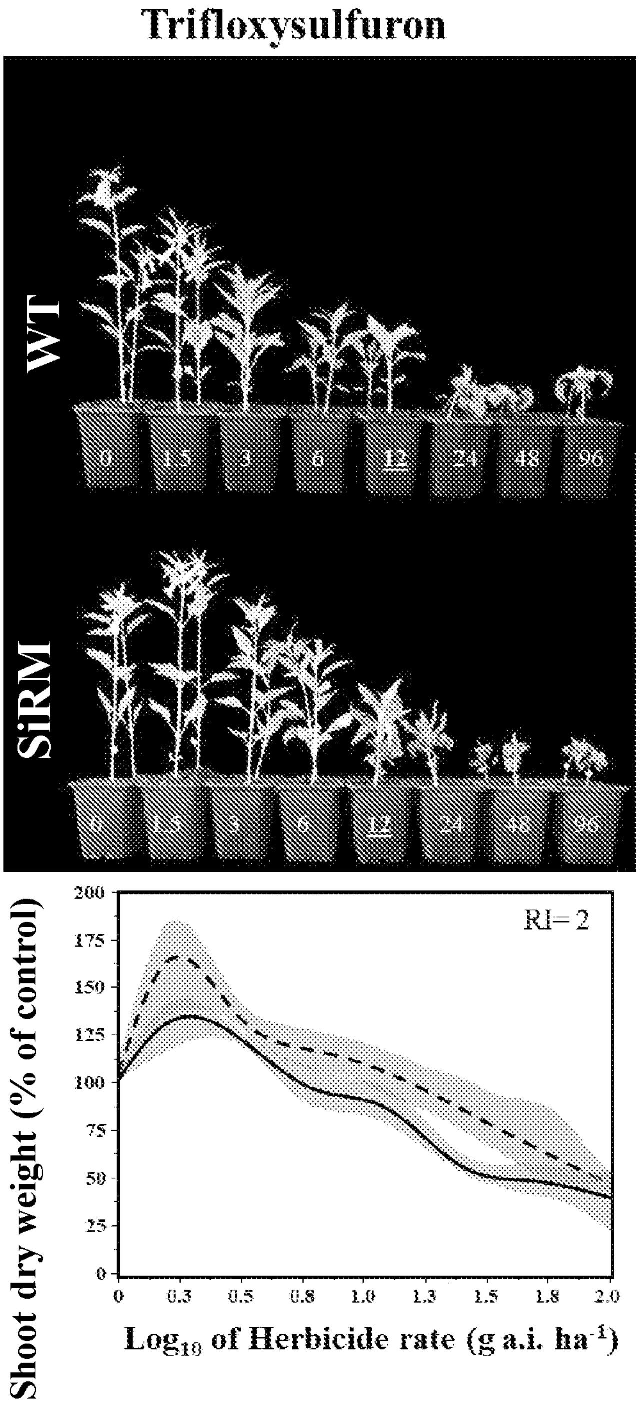
Figure 7B:
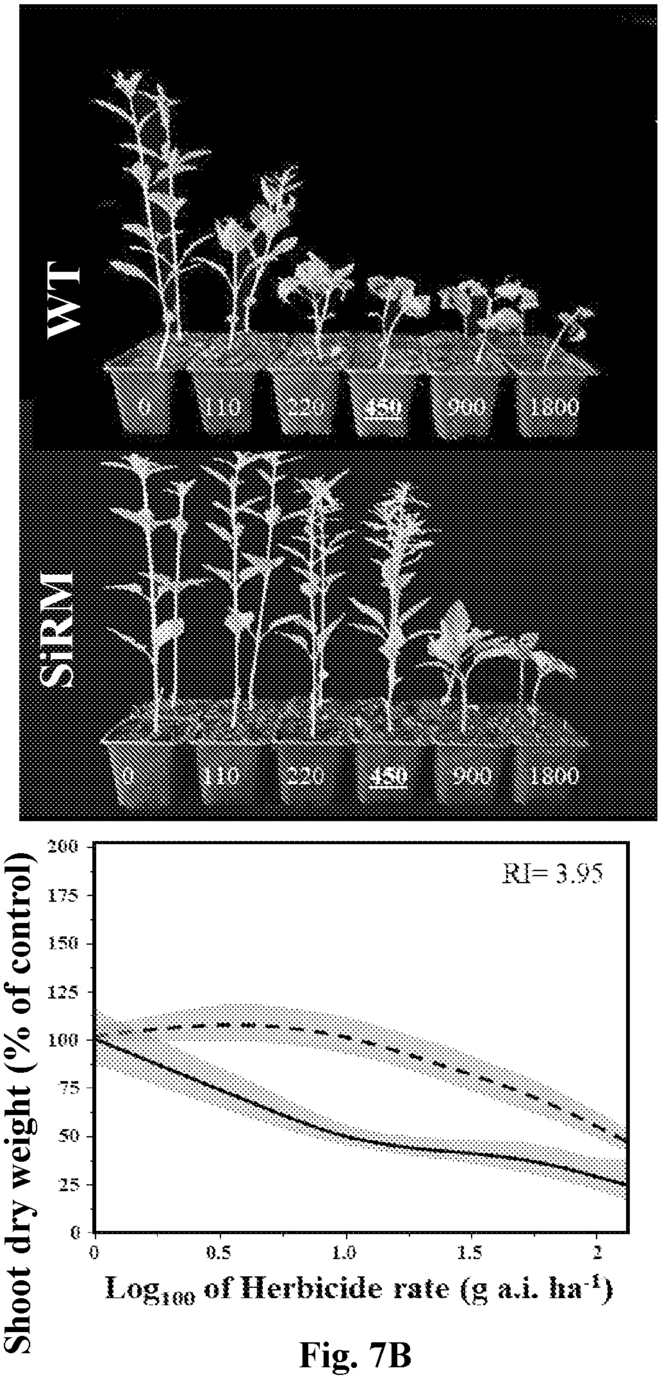
Figure 7C:
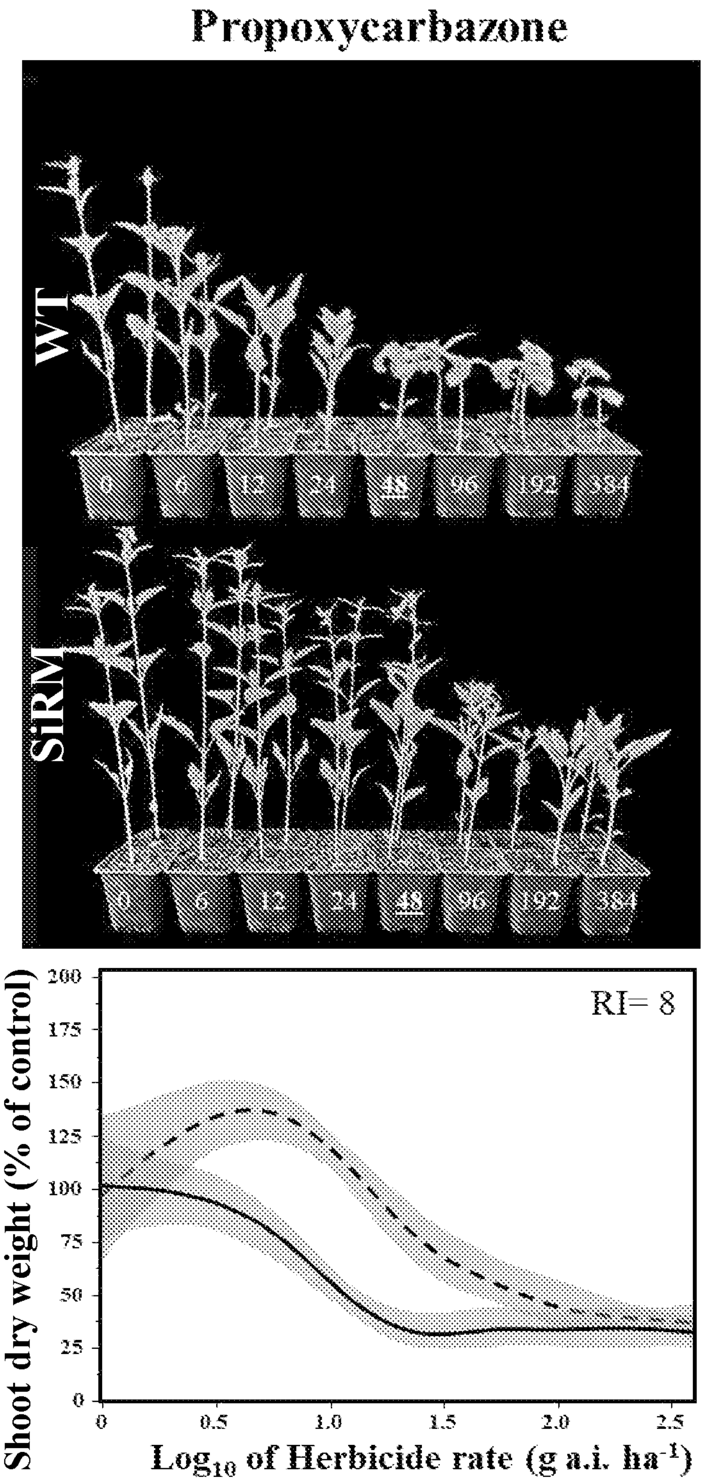
Figure 7D:
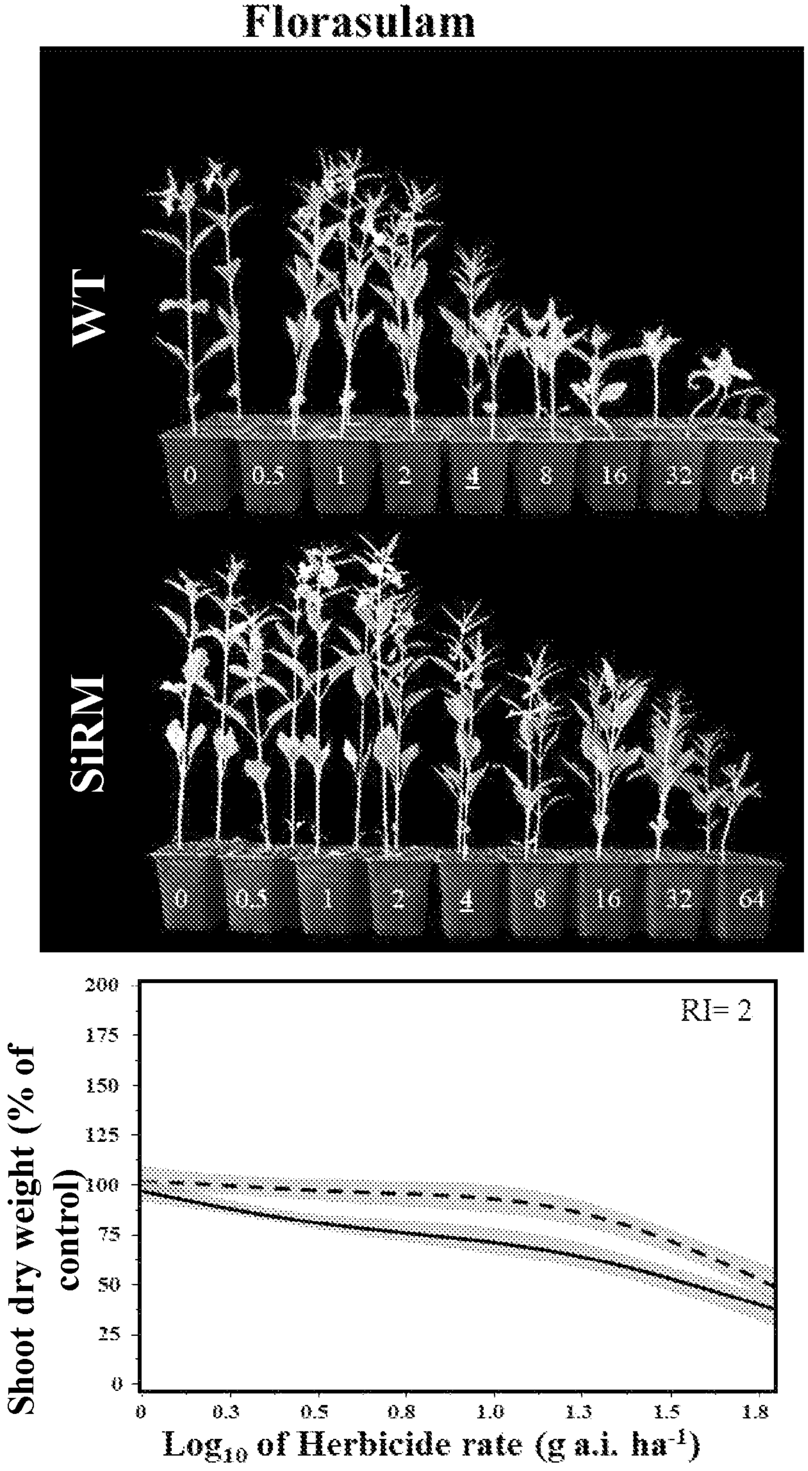
Figure 7E:
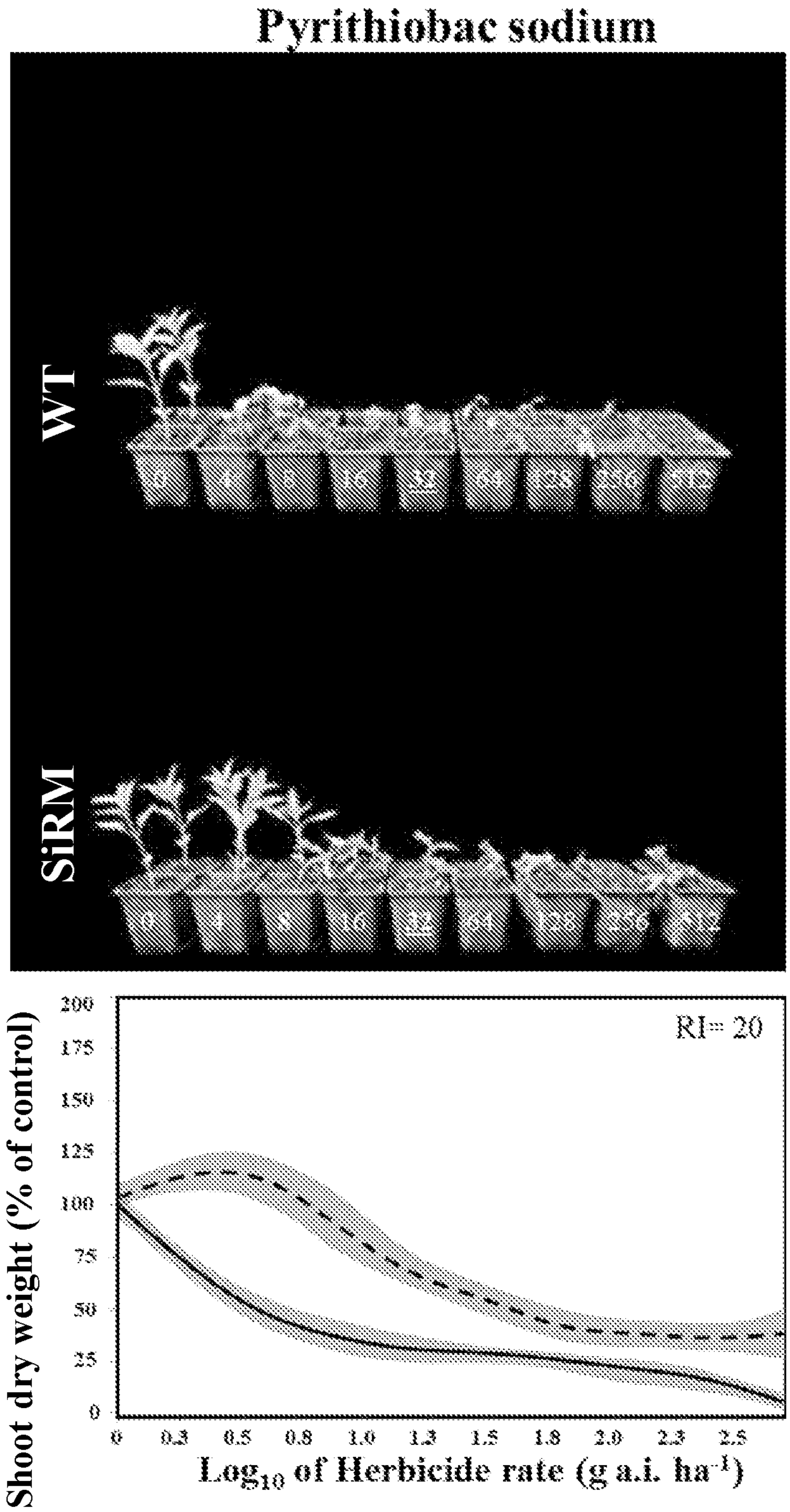

To test if the point-mutation in the SiALS gene affects sesame plant response to other herbicides of the ALS class, a dose-response assays for the additional classes was performed. Overall, for all herbicides applied, SiRM plants showed better performance compared with WT plants, as reflected in their higher $ED_{50}$, and a higher growth rate at the field dose level (Table 3). Application of two sulfonylurea (SU) herbicides, foramsulfuron, and trifloxysulfuron exposed mild resistance of the SiRM plants as compared with WT plants. Under the recommended dose, WT plants exhibited significant reduction compared with SiRM in shoot DW (63% vs. 18% and 25% vs. 8% for trifloxysulfuron and foramsulfuron, respectively) and shoot length (74% vs. 7% and 64% vs. 58%) (FIG. 7A-B). The application of increasing doses of propoxycarbazone resulted in a severe response of the WT plants already at a low dose of ⅛X, whereas the SiRM plants were able to maintain growth (and develop flowering buds) up to the recommended dose (FIG. 7C). Application of florasulam (triazolopyrimidines class) showed a similar response of both lines under low doses, with a mild advantage of the SiRM line under higher doses, as also reflected in RI=2 (Table 3; FIG. 7D). Application of pyrithiobac sodium was lethal for both lines, with the mutant able to survive up to the recommended dose (however, with a severe reduction of shoot length of 66%) (Table 3; FIG. 7E).

TABLE 3

Effect of different ALS inhibitors application at field rates on wild type (S-416) and SiRM plants

| | $ED_{50}$ | | Shoot DW field rate (% control) | | Shoot length field rate (% control) | | |
|---|---|---|---|---|---|---|---|
| Herbicide | WT | SiRM | WT | SiRM | WT | SiRM | RI |
| Imazamox | 18 | 823 | 0.28 | 1.02 | 0.33 | 1.01 | 45 |
| Imazapic | 236 | 563 | 0.74 | 0.75 | 0.35 | 0.94 | 2.4 |
| Imazethapyr | 3.7 | 161 | 0.17 | 0.78 | 0.27 | 0.87 | 48 |
| Foramsulfuron | 41 | 165 | 0.37 | 0.82 | 0.26 | 0.93 | 3.95 |

TABLE 3-continued

Effect of different ALS inhibitors application at field rates on wild type (S-416) and SiRM plants

| | $ED_{50}$ | | Shoot DW field rate (% control) | | Shoot length field rate (% control) | | |
|---|---|---|---|---|---|---|---|
| Herbicide | WT | SiRM | WT | SiRM | WT | SiRM | RI |
| Florasulam | 31 | 62 | 0.81 | 0.71 | 0.60 | 0.83 | 2 |
| Pyrithiobac sodium | 9.8 | 202 | 0.26 | 0.65 | 0.17 | 0.34 | 20.5 |
| Propoxycarbazone | 12 | 96 | 0.42 | 0.50 | 0.30 | 0.80 | 8 |
| Trifloxysulfuron | 33 | 69 | 0.75 | 1.05 | 0.36 | 0.42 | 2 |

Table 3: Shoot dry weight (DW) and shoot length as a percentage of that of the untreated control (UTC) and $ED_{50}$ values (herbicide rate reducing plant growth by 50%) are presented. Values are means (n=5).

Example 6: The SiRM Plants Exhibited High Resistance to Pre-Emergence Imazapic Application To evaluate the response of SiRM plants to the pre-emergence application of Imazapic, a responsiveness assay at increasing doses (48, 96, and 144 g a.i. $h^{-1}$) was performed. In general, under all tested doses, the SiRM plants exhibited normal growth and development (100% survival rate; FIG. 6A). To test the potential of using Imazapic pre-emergence, the WT and SiRM plants and two weed species *A. palmeri* and *Euphorbia heterophylla*, were compared under the highest dose (144 g a.i. $h^{-1}$) using visual and image-based phenomics approaches (FIG. 6B). While WT plants were fully controlled and did not develop beyond the growth of the cotyledons, the SiRM plants developed normally without any visual differences compared to the untreated control. These differences were also expressed belowground when the WT plants did not develop roots (82 vs. 5 mm under controlled and Imazapic treatment, respectively), while SiRM maintains a similar root length (72 vs. 85 mm, respectively, P=0.106) (FIG. 6B). The canopy coverage of the WT plants 14 days after sowing showed a significant reduction (2.23 vs. 0.27% of coverage, P=0.0008), while SiRM plants maintained similar values (FIG. 6C).

ALS herbicides are known to have a strong effect on the root developments due to their phloemic transport to the meristems (sink organs), as was also found here (FIG. 6B). The higher root length found in the treated SiRM seedlings leads us to investigate the possibility of roots hormesis response. However, the pre-emergence Imazapic application at increasing doses didn't show any significant differences in root volume (FIG. 6C).

Example 7: Effect of the Mutation of ALS Configuration

FIG. 8 shows that substitution from Alanine to Valine changes the protein conformation at the binding site of the herbicide and decreases the affinity of the herbicide to the ALS enzyme.

Example 8: 2021 Field Trial-Effect of Imazapic on Weed Control and Sesame Performance Under the control treatment (herbicide-free) the *A. palmeri* was the dominant weed (98 plants per plot), and no other weeds or sesame plants were able to develop as displayed visually (FIG. 9A-C). The pre-application of Imazapic resulted in weed-free plots. The A. *Palmeri* didn't emerge (full-control), and the *Abutilon* plants that emerged didn't develop beyond the cotyledons. As is clearly shown in FIG. 9 D-E, pre-application of Imazapic had no deleterious effects on the resistant plants of the invention, showing similar growth to the growth obtained in the weed-free control. Pre-application of Imazapic also resulted in reduced height to the first capsule, which indicates a decrease in apical meristem dominance (FIG. 9E-G).

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. A sesame (*Sesamum indicum* L.) plant or a part thereof comprising at least one cell comprising a mutant acetolactate synthase encoding polynucleotide (mALS), wherein the mALS encodes a mutant acetolactate synthase (mALS) protein having a reduced affinity to at least one acetolactate synthase (ALS)-inhibiting herbicide compared to a wild-type *S. indicum* ALS (SiALS) protein, wherein the mALS protein comprises an amino acid sequence having at least 95% identity to the amino acid sequence set forth in SEQ ID NO: 1 and comprising the amino acid valine at position 188, and wherein the plant is resistant to at least one ALS-inhibiting herbicide.

2. The sesame plant of claim 1, wherein the mALS protein comprises the amino acid sequence set forth in SEQ ID NO:3.

3. The sesame plant of claim 1, wherein the mALS protein is encoded by a polynucleotide comprising a substituted codon coding for an amino acid valine at positions 562-564, the polynucleotide comprising a nucleic acid sequence having at least 90% identity to the nucleic acid sequence set forth in SEQ ID NO:2.

4. The sesame plant of claim 3, wherein the polynucleotide comprises the nucleotide thymine (T) at position 563 of a nucleic acid sequence having at least 90% identity to the nucleic acid sequence set forth in SEQ ID NO:2.

5. The sesame plant of claim 4, wherein the polynucleotide comprises the nucleic acid sequence set forth in SEQ ID NO:4.

6. The sesame plant of claim 1, wherein said plant is characterized by indehiscent capsules and wherein the indehiscent capsules are visibly closed when fully ripe.

7. The sesame plant of claim 1, wherein said plant produces higher seed yield when grown under weed-free conditions obtained by applying ALS-inhibiting herbicide compared to when grown under weed-free conditions obtained by alternative weed control methods, wherein the herbicide is applied post-emergence.

8. The sesame plant of claim 1, wherein the mALS encoding polynucleotide is an exogenous polynucleotide.

9. The sesame plant of claim 1, wherein the ALS-inhibiting herbicide is of a type selected from the group consisting of herbicidal effective Imidazolinones (IMI), Sulfonylureas (SU), Pyrimidinylthiobenzoates (PTB), Triazolopyrimidines (TP), and Sulfonylaminocarbonyltriazolinone (SCT).

10. A seed of the sesame plant of claim 1, wherein a sesame plant grown from the seed comprises at least one cell comprising a mutant acetolactate synthase encoding gene (mALS), wherein the mALS encodes a mutant acetolactate synthase (mALS) protein having a reduced affinity to at least one ALS-inhibiting herbicide compared to a wild-type *S. indicum* ALS (SiALS) protein, the mALS protein comprising an amino acids sequence having at least 95% identity to the amino acid sequence set forth in SEQ ID NO: 1 and comprising the amino acid valine at position 188, and wherein the plant is resistant to at least one ALS-inhibiting herbicide.

11. An isolated cell or a tissue culture of the sesame plant or part thereof according to claim 1, wherein a sesame plant regenerated from the cell or tissue culture comprises at least one cell comprising a mutant acetolactate synthase encoding gene (mALS), wherein the mALS encodes a mutant acetolactate synthase (mALS) protein having a reduced affinity to at least one ALS-inhibiting herbicide compared to a wild-type *S. indicum* ALS (SiALS) protein, the mALS protein comprising an amino acids sequence having at least 95% identity to the amino acid sequence set forth in SEQ ID NO:1 and comprising the amino acid valine at position 188, and wherein the plant is resistant to at least one ALS-inhibiting herbicide.

12. A method for producing a sesame plant having tolerance and/or resistance to at least one ALS-inhibiting herbicide, the method comprising introducing at least one mutation in at least one allele of the plant endogenous ALS encoding gene, wherein the at least one mutation results in an encoded ALS protein comprising an amino acids sequence having at least 95% identity to the amino acid sequence set forth in SEQ ID NO: 1 and comprising the amino acid valine at position 188, characterized by a reduced affinity to at least one ALS-inhibiting herbicide compared to an ALS protein encoded by a non-mutated gene, thereby producing the sesame plant having tolerance and/or resistance to at least one ALS-inhibiting herbicide.

13. An isolated polynucleotide encoding acetolactate synthase (ALS) protein having a reduced affinity to at least one ALS-inhibiting herbicide compared to a wild-type *S. indicum* ALS protein, wherein the encoded ALS protein has at least 95% identity to the amino acid sequence set forth in SEQ ID NO:1 and comprising the amino acid valine at position 188.

14. The isolated polynucleotide of claim 13, wherein the encoded ALS protein comprises an amino acid other than alanine at position 188 of a protein having at least 90% identity to the amino acid sequence set forth in SEQ ID NO:1.

15. A method for producing a sesame plant having tolerance and/or resistance to at least one ALS-inhibiting herbicide, the method comprising introducing into at least one cell of a sesame plant susceptible to ALS-inhibiting herbicide at least one polynucleotide according to claim 13, thereby producing a sesame plant having tolerance and/or resistance to at least one ALS-inhibiting herbicide.

16. A method for identifying a sesame plant having an enhanced tolerance and/or resistance to at least one type of ALS-inhibiting herbicide, the method comprising detecting, in a genetic material obtained from the plant, the presence of a nucleic acid marker amplified by a pair of primers comprising the nucleic acid sequence set forth in SEQ ID NO:5 and SEQ ID NO:6.

17. A method for controlling weeds in the vicinity of at least one sesame plant resistant to at least one ALS-inhibiting herbicide according to claim 1, the method comprises applying at least one ALS-inhibiting herbicide to the weeds and said at least one sesame plant in an amount sufficient to inhibit the weed growth.

* * * * *